(12) United States Patent
Tajima

(10) Patent No.: US 7,014,814 B2
(45) Date of Patent: Mar. 21, 2006

(54) SUPPORT FOR SUBSTANCES FOR DETECTION, APPARATUS FOR PROCESSING SAME, METHOD OF PROCESSING SAME, APPARATUS FOR MAKING SAME, AND METHOD OF MAKING SAME

(75) Inventor: Hideji Tajima, Inagi (JP)

(73) Assignee: Bio Strand, Inc., Pleasanton, CA (US)

( * ) Notice: Subject to any disclaimer, the term of this patent is extended or adjusted under 35 U.S.C. 154(b) by 577 days.

(21) Appl. No.: 09/813,707

(22) Filed: Mar. 21, 2001

(65) Prior Publication Data

US 2001/0038808 A1 Nov. 8, 2001

Related U.S. Application Data

(60) Provisional application No. 60/192,205, filed on Mar. 27, 2000.

(51) Int. Cl.
*G01N 21/64* (2006.01)

(52) U.S. Cl. .................... 422/55; 422/68.1; 422/82.05; 422/82.06; 422/82.07; 422/82.08; 436/518; 436/527; 435/5; 435/6; 435/91.1; 435/91.2

(58) Field of Classification Search ................ 436/518, 436/527; 435/5, 6, 91.1, 91.2; 422/55, 68.1, 422/82.05, 82.06, 82.07, 82.08
See application file for complete search history.

(56) References Cited

U.S. PATENT DOCUMENTS

| | | | | |
|---|---|---|---|---|
| 6,037,186 A | * | 3/2000 | Stimpson | .................... 436/518 |
| 6,040,191 A | * | 3/2000 | Grow | .......................... 436/172 |
| 6,057,100 A | * | 5/2000 | Heyneker | ...................... 435/6 |
| 6,482,593 B1 | * | 11/2002 | Walt et al. | ...................... 435/6 |
| 6,649,404 B1 | * | 11/2003 | Vann et al. | .............. 435/288.7 |
| 6,653,151 B1 | * | 11/2003 | Anderson et al. | ........... 436/518 |

FOREIGN PATENT DOCUMENTS

| | | |
|---|---|---|
| JP | 48-39091 | 8/1973 |
| JP | 58-31998 | 2/1983 |
| JP | 04-112785 | 4/1992 |
| JP | 06-153996 | 6/1994 |
| JP | 11-64322 | 3/1999 |

* cited by examiner

Primary Examiner—Jill Warden
Assistant Examiner—LaToya Cross
(74) Attorney, Agent, or Firm—Haynes and Boone, LLP

(57) ABSTRACT

The present invention relates to a support for substances for detection, an apparatus for processing same, a method of processing same, an apparatus for making same, and a method of making same. The object of the present invention is to provide a reliable and high quality technology that can perform a series of processes, consistently, automatically and easily. A support for substances for detection of the present invention is constructed so as to comprise a flexible base member formed to be slender like a thread, string or tape, a variety of substances for detection having predetermined chemical structures and being fixed side by side along the length of the base member, and a supporting member for supporting the base member in a manner that enables expansion, wherein a fixed location of each substance for detection corresponds with the chemical structure thereof.

13 Claims, 13 Drawing Sheets

Fig. 1
(a)
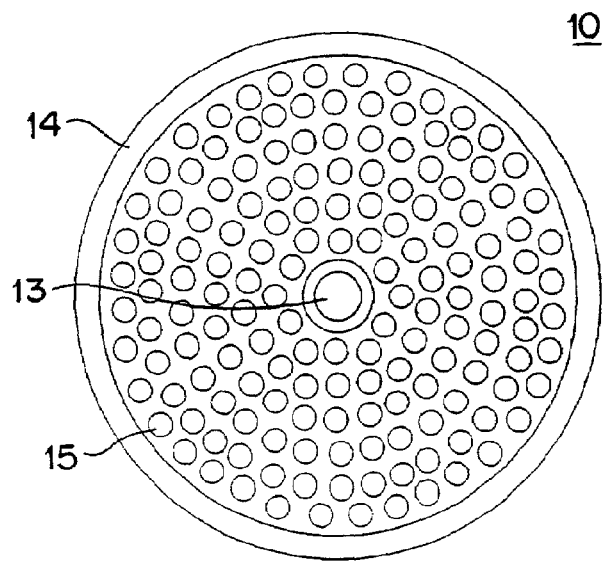
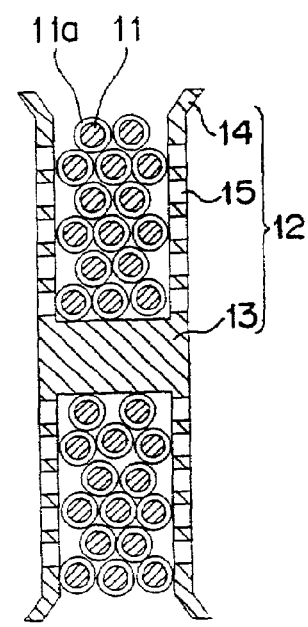
(b)
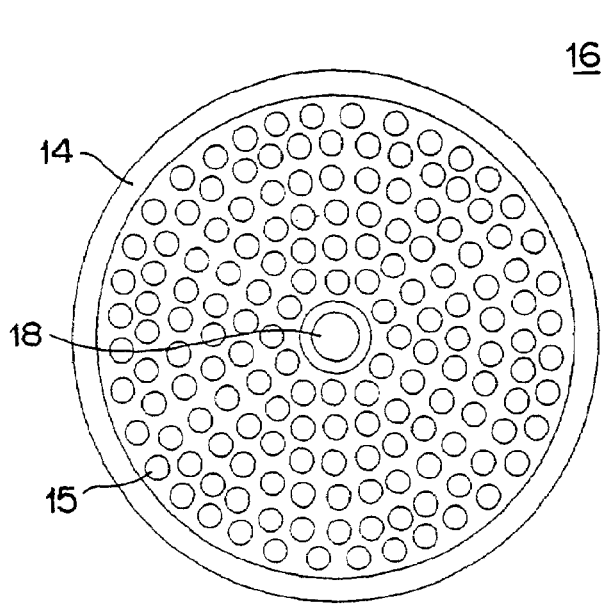
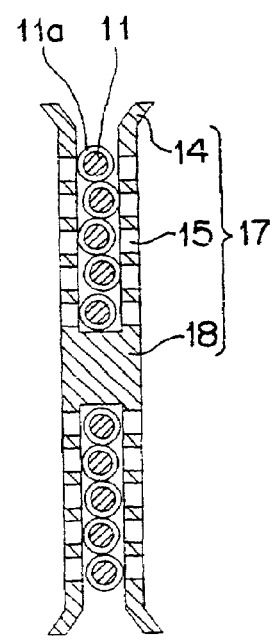

Fig. 2
(a)
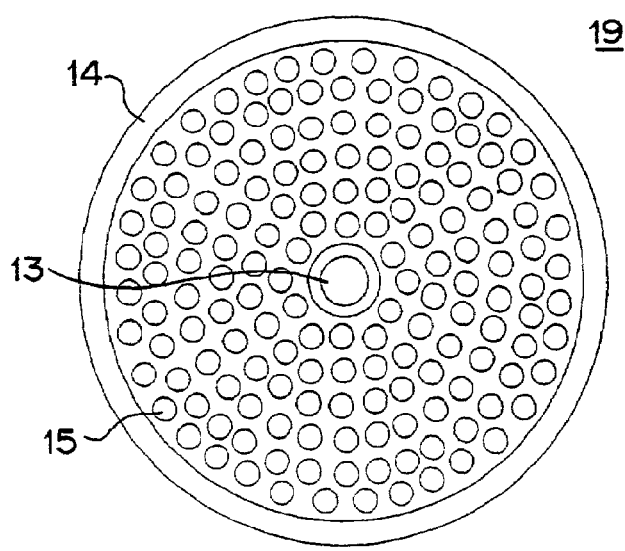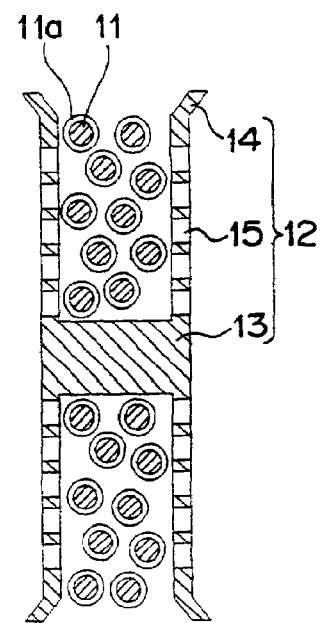
(b)
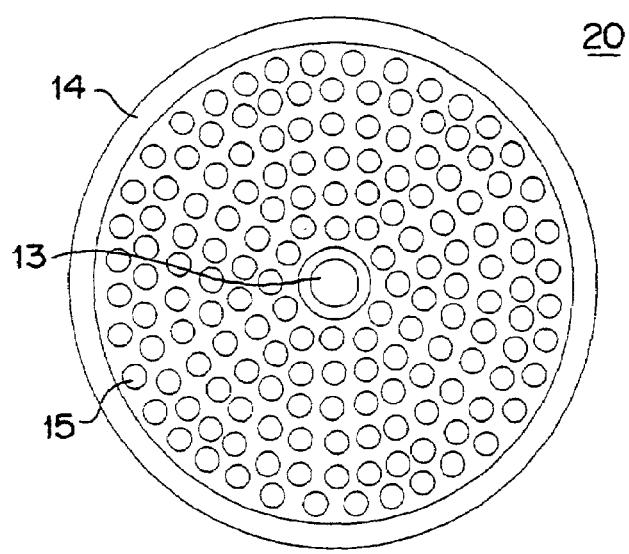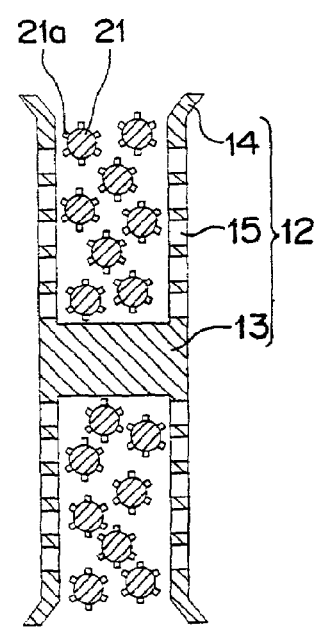

Fig. 8
(a)
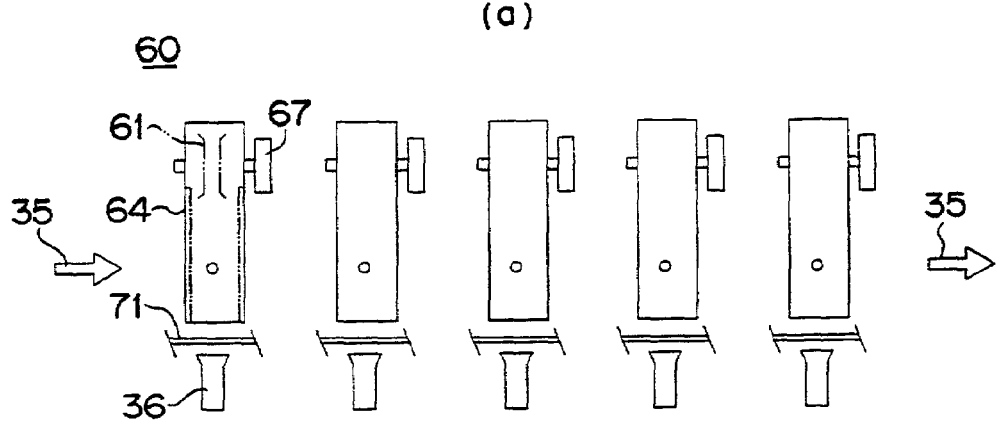
(b)
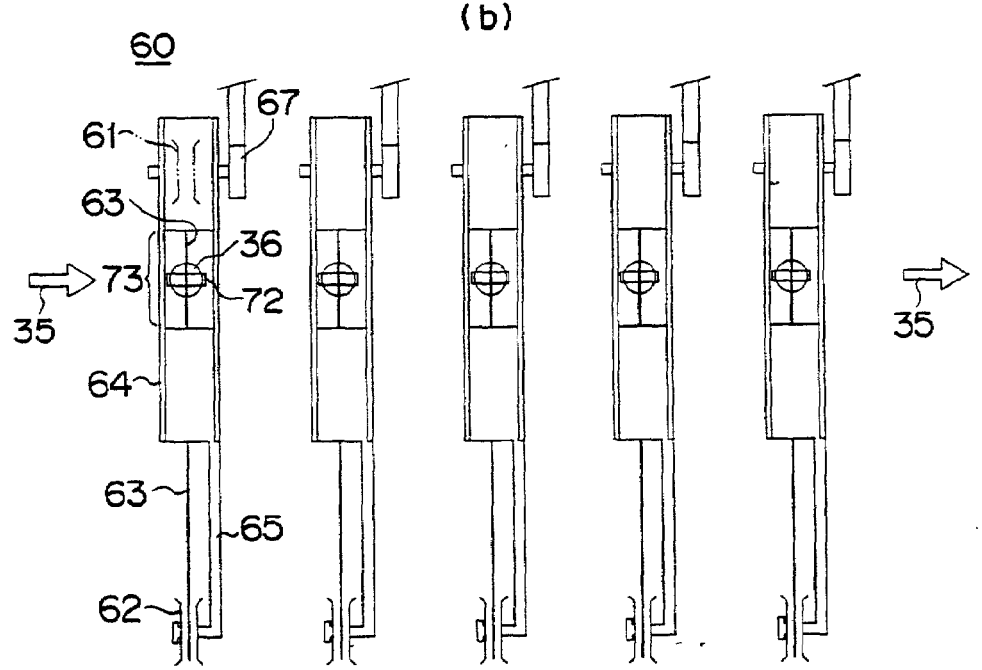

Fig. 15
(a)
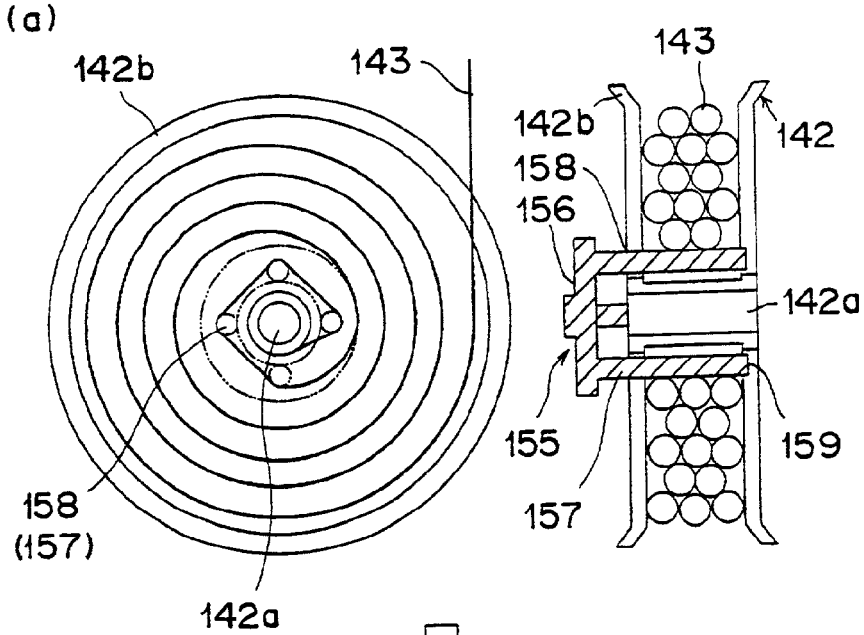
(b)
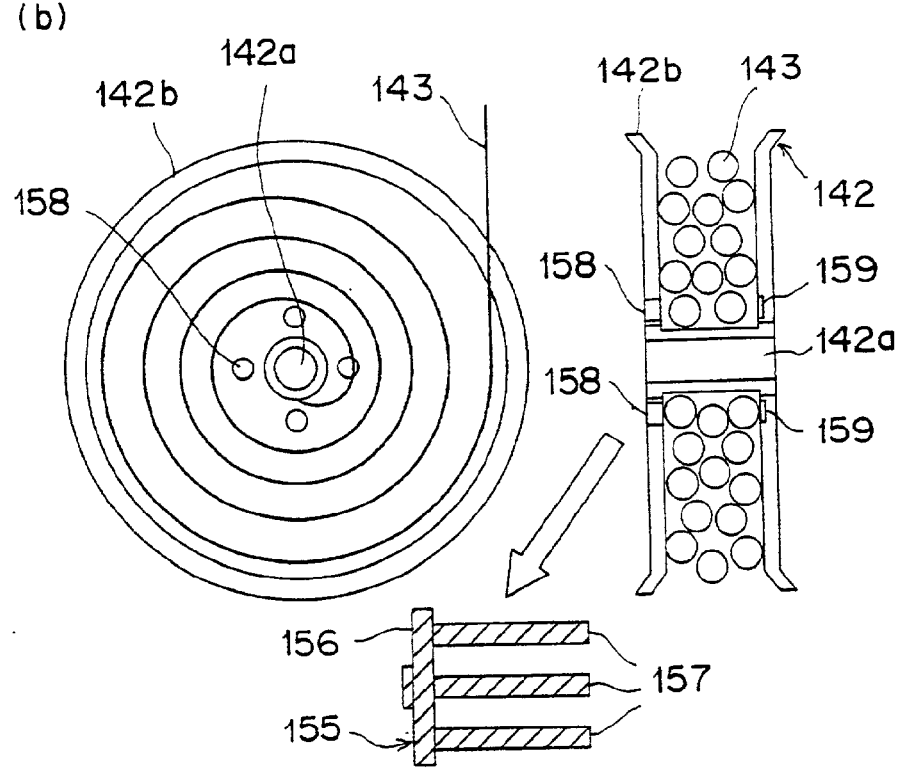

SUPPORT FOR SUBSTANCES FOR DETECTION, APPARATUS FOR PROCESSING SAME, METHOD OF PROCESSING SAME, APPARATUS FOR MAKING SAME, AND METHOD OF MAKING SAME

CROSS-REFERENCE TO RELATED APPLICATION

This application claims the benefit of U.S. Provisional Patent Application, Ser. No. 60/192,205, filed Mar. 27, 2000.

BACKGROUND OF THE INVENTION

1. Field of the Invention

The present invention relates to a support for substances for detection, an apparatus for processing same, a method of processing same, an apparatus for making same, and a method of making same. Particularly, the present invention relates to all manner of fields which require inspection, analysis and examination of biopolymers such as genes, immune system, proteins, amino acids, and sugars; including the fields of engineering, agricultural science incorporating foodstuffs, agricultural production, and fish processing, pharmaceuticals, the medical field incorporating hygiene, health, immunity, disease, and scientific field such as chemistry and biology.

Particularly, the present invention relates to a support for substances for detection, an apparatus for processing same, a method of processing same, an apparatus for making same, and a method of making same which are suitable for analysis of genes, including mutation analysis, polymorphism analysis, mapping, base sequence analysis, and mechanism analysis.

2. Description of the Related Art

Currently, determinations of gene base sequences use a DNA chip wherein an oligonucleotide with a predetermined base sequence is attached to a substrate at a predetermined position. DNA chips require the preparation of a known oligonucleotide array, which is a flat surface comprising a semiconductor film or a slide glass, on to which is spotted a minute quantity of suspensions of a plurality of different, known oligonucleotides, with the oligonucleotides fixed in an array patten sequence.

In order to form a plurality of oligonucleotides on the restricted surface area of a DNA chip, it is necessary for a human operator to use a dispensing apparatus and then dispense spot by spot a minute quantity of each oligonucleotide suspension onto the surface leaving a predetermined separation between adjacent spots, while avoiding cross-contamination. This DNA chip is used for various analyses and examinations of genes.

Currently, in order to determine, for instance, base sequences of an unknown target gene, a user dispenses a liquid suspending the target gene marked by luminous substance, onto the DNA chip. Then at an interval of a certain reaction time, the user removes the remnant suspension by cleaning. Thereafter, the user determines the base sequence according to the locations where light emission is detected in the DNA chip.

In order to manufacture DNA chips, many types of oligonucleotides must be densely positioned plane-like in a small region. The more densely the oligonucleotides are positioned, the more closely they approach one another. Therefore, not only cross-contamination is likely to occur, but also an amount of oligonucleotide in each fixed location reduces much more.

Particularly, the reduction of the amount of oligonucleotide causes problems in that determination of locations where light emission is detected tends to include errors and inaccuracy.

Furthermore, the reduction of the amount of oligonucleotide causes problems in that the encounter rate and efficiency of reaction are lowered and it takes a long time for processing.

Further, due to plane-like arrangement of samples, there are problems in that the more densely samples are positioned, the more difficult handling and automation becomes.

Therefore, manufacturing the DNA chip requires much labor and a long time, and there is a problem in that the cost of production of DNA chips increases. Particularly, in order to analyze, examine and determine the structure of unknown target substances including an enormous amount of base sequences, the analysis, examination and so on of a large number of DNA chips is necessary.

Consequently, the present invention aims to resolve the problems outlined above. A first object is to provide a reliable and high quality support for substances for detection, an apparatus for processing same, a method of processing same, an apparatus for making same and a method of making same.

A second object is to provide a support for substances for detection, an apparatus for processing same, a method of processing same, an apparatus for making same and a method of making same which can perform a series of processes consistently, automatically and easily.

A third object is to provide a reliable and efficient support for substances for detection, an apparatus for processing same, a method of processing same, an apparatus for making same and a method of making same which can increase efficiency of reaction and encounter rate between substances for detection and target substances.

A fourth object is a support for substances for detection, an apparatus for processing same, a method of processing same, an apparatus for making same and a method of making same which can readily, easily, and inexpensively be made in large quantity.

SUMMARY OF THE INVENTION

In order to resolve the above problems, a first aspect of the invention is a support for substances for detection comprising a flexible base member formed to be slender like a thread, string or tape, a variety of substances for detection having predetermined chemical structures and being fixed side by side along the length of the base member, and a supporting member for supporting the base member in a manner that enables expansion, wherein a fixed location of each substance for detection corresponds with the chemical structure thereof.

In this description, "substance for detection" refers to a substance which is to be detected, for example, biopolymer like gene substances such as DNA, RNA and oligonucleotides, proteins, amino acids, and sugars, in order to either determine a structure of an unknown substance, or perform various analysis or examination of the target substances. When the substance for detection is a gene, "chemical structure" means a basic sequence.

The "base member" is made of a flexible material. The material includes for example, organic matters such as polyethylene, polystyrene, polypropylene and urethane, inorganic matter such as glass fibers, ceramics, metals, or materials combined between organic matters and inorganic matters such as a film or tape made of organic matter spread with ceramic fine particles.

The base member includes a member, whose surface is covered with or is processed by or which is made of, materials for fixation such as hydroxyl group, amino group, carboxyl group, epoxy group, biotin or avidin.

Suitable techniques for supporting the base member to the supporting member include winding on a core, flat winding to produce a flat plane without cores, routing through one or more posts mounted in a plate, folding in, mounting, laminating or arranging. Alternatively, these include solid winding, lamination, or arrangement or folding to form a cylinder, a prism, a circular cone, a pyramid or a sphere.

Further, these include integration of neighboring sides thereof with each other, or by forming a space between these, or by sandwiching auxiliary members. The techniques to wind the base members may include not only winding while being aligned, but also loosely or irregularly winding without being aligned. In short, transformation between integration and expansion can easily and reliably be performed. Furthermore, when detection is carried out in an integrated state, locations of the substances for detection must be able to be specified.

With regard to a DNA chip, it is very difficult to position the substances for detection by dispensing etc. at correct locations, densely and 2-dimensionally from the beginning. This is because the fixed locations are closely gathered together. In contrast, with the present invention, after the substances for detection, for example, oligonucleotides are closely fixed on a base member in a one-dimensional state where the base member is expanded (first integration), then the base member is integrated by closely winding (second integration). Consequently, a support for substances for detection having a high integration can be obtained.

With the present invention, the integration process can be divided into two processes and the density in each process need not be high. Therefore, the interval between fixed locations in the first integration process of the present invention can be wider that in the case when the fixed locations are arranged plane-like from the beginning. Thus, each amount of substances for detection to be fixed can be larger than the case when the fixed locations are arranged plane-like from the beginning. It thus follows that efficiency of reaction, encounter rate, and accuracy of measurement can be improved.

The base member of the present invention is formed to be a long and slender solid body. Therefore, though an area projected in a predetermined direction is equal, the surface area in an expanded state, is much larger than that in an integrated state. Further, when the base member is expanded, processes can be easily performed, and locations can be specified by detection more easily than in the case of the integrated state.

Further, cavity sections such as trenches and holes having a bottom or no bottom, or, holding sections having foam materials, porous materials, fibrous materials, uneven materials or impregnating materials may be mounted in the base member.

The "cavity sections" include, for example, trenches or holes mounted in a side section or an upper section or convexities and concavities mounted in a side section or an upper section. The "holding sections" refers to those which can absorb or hold a liquid, and which are made of for example, paper, cloth, threads, strings, made of organic materials such as polyethylene, polystyrene, polypropylene, urethane, or made of inorganic materials such as glass, ceramics and metal.

The "materials having an uneven surface" means such materials that seem to be smooth at a glance, but that have many minute concavities and convexities or ciliary bodies overall, or in the side or upper sections. The materials having an uneven surface are for example, such strings, threads or tapes made of organic materials on which minute ceramic particles are spread. Since base members made of the materials having an uneven surface have characteristics that contact between surfaces of the base member generates adhesion between these, such materials can be used for combining the integrated base member.

Needless to say the base members may be those having an even surface which is free of the cavity sections or holding sections.

Further, the cavity sections or holding sections may be arrayed in the direction of the length of the base member. Furthermore, the holding sections may include base members such as those made of foam materials, porous materials, fibrous materials, or impregnation materials.

Furthermore, in the case where the substances for detection are positioned in the holding sections or the cavity sections, they may be fixed by adjusting the viscosity thereof.

The amount of substances for detection held in those cavity sections or holding sections, can generally be larger than the amount of those held in locations free from the cavity sections or holding sections. Consequently, when the reaction process is performed, the encounter rate between substances can be improved and efficiency of reaction and accuracy of detection can be improved.

As mentioned above, with the first aspect of the invention, a long and slender base member which is in an expanded state at first, is supported on a supporting member of the support for substances for detection, in such a manner that enables or prevents expansion. Consequently, since according to necessity, the expanded state or integrated state can arbitrarily chosen for the base member, the processes can be performed in an optimum state. Consequently, the present invention can speed up processes, improve efficiency, facilitate the processes, and improve reliability.

For instance, the process for positioning and fixing substances for detection, the process for reaction, and the process for detection can be sped up, improved in efficiency, facilitated, and improved in reliability, by executing positioning, fixation and detection of each substance for detection in each location, in an expanded state.

Particularly even if the substances for detection are not densely positioned and fixed, in the state with the base member expanded, high density can be obtained by integrating the base members. Consequently the process for positioning, fixation and reaction can be facilitated.

Furthermore, with the present invention, instead of directly handling the thin and slender minute base member, the supporting member for the base member is mounted and handled and the base member is stored, processed, and transferred, with the base member supported by the supporting member. Therefore, considering that the supporting member for the base member is larger, more rigid, more compact, and more stable than the base member, handling and protection of the base member is facilitated.

Furthermore, the present invention utilizes base members that have a substantially minute solid structure. Therefore, for the same overall volume, the surface of the minute solid structure is much larger than one that utilizes only a plane.

Hence the amount of substances for detection at each fixed location can be increased, and the efficiency of reaction and detection can be improved.

A second aspect of the present invention is a support for substances for detection according to the first aspect of the invention, wherein one or more marks are provided on the base member to indicate a reference position.

For example, a luminous substance such as a fluorescent substance is used as a "mark". The mark is used not only to indicate the reference position on the base member, but also to distinguish target substances from other substances. The latter mark includes for example, marking substances such as luminescent substances that are combined with the target substances. Further, such substances for detection that are adhered to polystyrene minute particles of substantially same size lined up and fixed to the base member, and covered with gold on only the upper hemisphere, may be included in the latter mark. In this case, when the substances for detection are contacted with the suspension incorporating the target substances while a white light is irradiated onto the surface, the colors of the particles are changed by combination with the target substances. Therefore, the fixed locations combined with the target substances are directly indicated by the detected color.

It is preferable that both of the mark for indication of the reference position and the mark for discrimination of the target substances can be clearly distinguished at the time of detection, by wave length, strength, polarized rate, phase or life span of the excitation ray or radiated ray.

With the second aspect of the invention, since the absolute locations on the base member can be easily and positively specified, the substances for detection can be surely and reliably specified.

A third aspect of the present invention is a support for substances for detection according to the first aspect or the second aspect, wherein the base member is supported by the supporting member, while being enclosed in a defined area so that the base member can contact with a liquid, and can be expanded from the area. It is preferable that the "area" is small and compact to cope with small amounts of liquid. For this area, a reel, or a drum is suitable. Further, the base member may be looped over one more posts mounted in a plate. The area is necessary for orderly integrating and expanding the base member without knots or tangles.

With the third aspect of the present invention, the base member is confined in a defined area so that it can contact with a fluid, and is supported so that it can expand from the area. Hence, reaction in a liquid suspending minute amount of a target substance can be carried out uniformly and evenly. As circumstances demand, change between the expanded state and the integrated state can easily be carried out. Further, as the base member is confined in a defined area, storing, processing and transferring etc. can be easily performed.

A fourth aspect of the present invention is a support for substances for detection, according to any one of the first to third aspects of the invention, wherein the supporting member comprises a reel, and the reel comprises a core on which the base member is wound, and two guide frames mounted on opposite ends of the core facing one another and through which liquid can pass.

On the "core", the base member maybe wound in alignment so as to have many layers and one row, or two or more rows and one or more layers, or may be wound without any alignment.

With the fourth aspect of the invention, since the reel is used as the member for support, expansion and take-up can be easily performed, and the storing, processing, or transferring can easily be performed.

A fifth aspect of the invention is a support for substances for detection according to any one of the first to fourth aspects of the invention, wherein the supporting member comprises a frame body, and a feed support section mounted on the frame body for supporting the base member in a manner that enables feeding, and the base member is supported by the feed support section so as to be able to travel along a defined feed pathway.

A sixth aspect of the invention is a support for substances for detection according to the fifth aspect of the invention, wherein the feed support section comprises a drum rotatably mounted on the frame body and threaded around a periphery thereof, and the frame body has an arm for enabling the base member to be inserted into a vessel outside of the support for substances for detection, and the base member is wound along a bottom of the thread of the drum and can be moved in the neighborhood of a tip end of the arm by rotating the drum.

With the fifth or the sixth aspects of the invention, since the base member is supported by the feed support section, the substances for detection fixed to the base member can be easily transferred by moving along the feed pathway. Therefore, automation can easily be realized.

Furthermore, the support for substances for detection, as well as the equipment relating to it, can be provided at low cost and in large quantities by standardization or normalization of the frame body. Since the base member can be processed variously or transferred with the support while being supported by the feed support section, the base member need not directly be touched and is protected.

Further, with these aspects of the invention, since the minute base member is fed, the process for transferring can be carried out more easily than for the case where the support for substances for detection itself is transferred.

A seventh aspect of the invention is a support for substances for detection according to the fifth aspect of the invention, wherein the feed support section comprises a supply reel and a take-up reel having a core around which the base member can be wound, and two guide frames through which liquid can pass mounted on opposite ends of the core, and two reels are rotatably mounted on the frame body, and the frame body has an arm for enabling the base member to be inserted into a vessel outside of the support for substances for detection, and the base member is routed between two reels so as to pass around the tip end of the arm.

With the seventh aspect of the invention, processing is facilitated since various processes can be carried out by feeding the base member between the reels, with only the lower end of the arm inserted into a vessel etc.

An eight aspect of the invention is a support for substances for detection, according to the seventh aspect, wherein the frame body comprises a casing, and an arm outwardly extending from the casing, and the take-up reel is rotatably mounted in the casing, and the supply reel is rotatably mounted on the tip end section of the arm. With the present invention, a roller etc. is not necessary in the tip end section of the arm.

With the eighth aspect of the invention, since the time for feeding the base members per se for reaction can be shortened by mounting the take-up reel on the tip end section of the arm, the time for the process for reaction can be shortened.

A ninth aspect of the invention is a support for substances for detection according to any one of the fifth to the eighth aspects, wherein the feed support section comprises one or more rollers rotatably mounted on the frame body along the feed pathway.

With the ninth aspect of the invention, since various feed pathways can be formed by mounting the rollers, various processes can be carried out. Furthermore, drying of the base member can simultaneously be carried out by absorption of a liquid with the roller.

A tenth aspect of the invention is a support for substances for detection according to the ninth aspect, comprising a protection belt sandwiched between the roller and the base member at the periphery of the roller, that travels in a predetermined feed velocity.

Preferably the "predetermined feed velocity" is set up to be substantially equal to a feed velocity of the base member, but is not limited to this case. Preferably "the protection belt" is formed so as to be larger than the base member in width and length.

With the present invention, the base member is not rubbed and damaged. Since the base member does not touch the roller, cross-contamination can be reliably avoided. Further, drying of the base member can be carried out by using a liquid absorbing material such as paper or cloth, as the protection belt.

An eleventh aspect of the invention is a support for substances for detection according to any one of the fifth to the tenth aspects, comprising a detection region and/or a reaction region, on the feed pathway of the base member, wherein the detection region is one where substances for detection are detected, and the reaction region is the one where reaction between the substances for detection and the target substances is carried out. Here "detection", is for example, optical detection.

With the present invention, processes can be automatically carried out consistently, by providing the detection region or the reaction region in a part of the feed pathway.

A twelfth aspect of the invention is a support for substances for detection according to any one of the fifth to the eleventh aspects of the invention, wherein the feed pathway of the base member forms a loop. With this aspect of the invention, reaction can be easily and rapidly performed, and detection can be reliably carried out by repetitively feeding the base member.

With the twelfth aspect of the invention, since the looped feed pathway for the base member is used, processes or measurement can be repeatedly performed merely by transferring in a predetermined direction, thus facilitating handling.

A thirteen aspect of the invention is a support for substances for detection according to any one of the fifth to the twelfth aspects, wherein the feed support section comprises a coupling for connecting with an outer feed mechanism for feeding the base member. The connection with the outer feed mechanism may be carried out, for example, by loading with the supporting member into a device comprising the feed mechanism.

With the thirteen aspect of the invention, since the coupling is mounted in the feed support, the base member can be easily fed by connecting the feed support and the feed mechanism, thus making handling easy.

A fourteenth aspect of the invention is a support for substances for detection according to any one of the third to the thirteenth aspects, wherein the supporting member is made of a permeable material having a plurality of pores.

With the fourteenth aspect of the invention, since the base member can be uniformly and evenly contacted with a liquid by using the supporting member made of the permeable material, processing for reaction can be uniformly and reliably performed.

The fifteenth aspect of the invention is a support for substances for detection according to the thirteenth aspect, wherein the supporting member comprises a spacer member for generating space around the base member, when the base member is integrated and supported.

As the spacer member of the supporting member, for example, protrusion sections inwardly extending from the guide frames of the supply reel, or the spacer member of the sixteenth aspect of the invention, are used so as to prevent sticking to the guide frames and to generate space between the base member and the guide frames.

A sixteenth aspect of the invention is a support for substances for detection according to the fifteenth aspect, wherein the spacer member comprises detachable pins provided so as to pierce through holes in one guide frame, pass near an outer periphery of the core and reach the other guide frame.

With this aspect of the invention, the base member is wound with the pins are mounted on the guide frames. After winding is completed, the pins are detached. Hence the base member is loosely wound and space is generated around the base member.

With the fifteenth and the sixteenth aspects of the invention, the base member can uniformly and evenly contact with a liquid by generating a space around the base member. Therefore, the processing for reaction can be uniformly and reliably performed.

A seventeenth aspect of the invention is an apparatus for processing a support for substances for detection, comprising a plurality of processing regions for carrying out various processes for reaction or detection of a support for substances for detection, an installing section for installing the support for substances for detection in a manner that enables dismounting, a transfer means for transferring the substances for detection between the processing regions, with the support for substances for detection installed in the installing section, and a control section for controlling so as to transfer the substances for detection in a predetermined order and in a predetermined timing.

Furthermore, a detection device for performing a detection in the detection region (processing region) of the feed pathway, may be mounted in the apparatus for processing the support for substances for detection.

With the seventeenth aspect of the invention, the process can be consistently and automatically performed with the support for substances for detection installed in the installing section, without being touched by humans.

An eighteenth aspect of the invention is an apparatus for processing a support for substances for detection according to the seventeenth aspect, wherein the transfer means transfers the substances for detection, together with the installing section.

With this aspect of the invention, when the substances for detection are transferred together with the installing section, the support for substances for detection is processed without being touched. Hence more reliable processing can be performed.

A nineteenth aspect of the invention is an apparatus for processing a support for substances for detection according to the eighteenth aspect, wherein the installing section comprises a container for holding the support for substances for detection, and the container is communicated with a small diameter section capable of being inserted into a processing region such as a vessel, and is detachably mounted in a dispensing device comprising a drawing/ discharging mechanism capable of adjusting the pressure in the container.

With the nineteenth aspect of the invention, since the process of the support for substances for detection is carried out by using the dispensing device, various and diverse processes can be carried out by drawing or discharging the liquid to or from the container holding the support for substances for detection. Further, complete processing including pre-processing can be consistently, efficiently and automatically performed by using the dispensing device for dispensing reagents etc. to each vessel, or for positioning a variety of substances for detection on the base members.

A twentieth aspect of the invention is an apparatus for processing a support for substances for detection according to the seventeenth aspect, wherein the installing section installs the support for substances for detection according to any one of the fifth to the sixteenth aspect of the invention so that the base member supported on the feed support section of the supporting member can be fed, and the transfer means transfers substances for detection between the processing regions, by feeding only the base member in the direction of the length, with the feed support section installed in the installing section.

With the twentieth aspect of the invention, only the base member of the support for substances for detection is fed in the direction of the length. Therefore, various processes can be easily carried out by only feeding the base member, thus facilitating processing and providing an overall compact processing apparatus.

A twenty first aspect of the invention is an apparatus for processing a support for substances for detection according to the twentieth aspect, wherein the transfer means comprises a feed mechanism connected to the feed support section of the support for substances for detection for feeding the base member.

Here "connecting" is performed, for example, by connecting between a coupling mounted on the core of the reel and a rotation drive means corresponding to the feed mechanism.

With the twenty-first aspect of the invention, since the base member can be fed by only connecting the support for substances for detection to the feed mechanism, the base member is not touched and handling is easy.

A twenty-second aspect of the invention is an apparatus for processing a support for substances for detection according to the seventeenth aspect, wherein the installing section installs the supporting member of the support for substances for detection according to any one of the fifth to sixteenth aspects of the invention, and the transfer means comprises an inter-region transfer means for transferring the supporting member between the processing regions together with the installing section, and a feed mechanism for feeding only the base member in the direction of the length with the supporting member installed in the installing section, and connected to the feed support section, and the substances for detection are transferred between processing regions, by using the inter-region transfer means and the feed mechanism.

With the twenty second aspect of the invention, the substances for detection are transferred by using the inter-region transferring means and the feed mechanism. Therefore, when a process that includes many steps is carried out, or large structure for the apparatus or large amount of space is necessary to perform the processing, the processing can be rationally and efficiently performed by separating the transferring step into two parts.

A twenty third aspect of the invention is an apparatus for processing a support for substances for detection according to any one of the seventeenth to twenty-second aspects, wherein vessels accommodating a variety of liquids are provided in the processing regions.

A twenty fourth aspect of the invention is an apparatus for processing a support for substances for detection according to the twenty-third aspect, wherein a thermostatic control means for controlling temperature in one or more vessels is installed in one or more vessels.

A twenty fifth aspect of the invention is an apparatus for processing a support for substances for detection according to the twenty-fourth aspect, further comprising a vibrating means for vibrating the vessel or the support for substances for detection in the vessel.

A twenty sixth aspect of the invention is an apparatus for processing a support for substances for detection according to any one of the twenty-third to twenty-fifth aspects, wherein one or more vessels accommodate a cleaning liquid.

A twenty seventh aspect of the invention is an apparatus for processing a support for substances for detection according to any one of the twenty-third to the twenty-sixth aspect, comprising a drying means for drying the support for substances for detection, in one of the processing regions.

A twenty eighth aspect of the invention is an apparatus for processing a support for substances for detection according to any one of the seventeenth to the twenty-seventh aspects, further comprising a detection means for detecting a change in the support for substances for detection. Here "change" includes light emission.

A twenty-ninth aspect of the invention is an apparatus for processing a support for substances for detection according to the any one of the seventeenth to twenty-eighth aspects, further comprising an analyzer for automatically designating relevant substances for detection on the basis of locations on the base member where a change such as light emission generated by a reaction with a suspension incorporating target substances is detected, and analyzing or examining a structure of the target substances on the basis of a structure or characteristics of the substances for detection.

Here "change such as light emission", occurs for example, in the case where any one of the substances for detection is reacted or combined a target substance marked with a luminous substance.

Further, this includes the case where a certain substance combined with the substances for detection changes color or generates light emission by combining or reacting with the target substances.

With the twenty-third to the twenty-ninth aspects of the invention, diverse and efficient processing can be carried out at the processing steps, by using various apparatus or performing various processes. Particularly, the process for reaction can be sped up by vibrating the support for substances for detection itself or the vessel.

A thirtieth aspect is a method of processing a support for substances for detection, comprising the steps of: installing a support for substances for detection in an installing section in a way that enables dismounting, transferring the substances for detection between a plurality of processing regions for processes of reaction or detection, and processing the support for substances for detection in each processing region, and a series of processes for the substances for detection are carried out by repeating the transferring step and the processing step.

Generally, the processing step includes a detecting step for detecting a change in the substances for detection.

Preferably the method further comprises a drying step for drying the base members before the detecting step. With the present invention, the processing can be consistently and automatically carried out with the support for substances for detection installed in the installing section, without human touch.

A thirty first aspect of the invention is a method of processing a support for substances for detection according to the thirtieth aspect, wherein the substances for detection are transferred together with the installing section, at the transferring step.

With the present invention, since the base member for detection can be transferred together with the installing section, the base member is minimally disturbed. Hence, more reliable processing can be carried out.

A thirty second aspect of the invention is a method of processing a support for substances for detection according to the thirtieth aspect, wherein at the transferring step the support for substances for detection is transferred together with an installing section, with the support installed into the installing section, and the installing section comprises a container for holding the support for substances for detection, and the container is communicated with a small diameter section capable of being inserted into a processing region such as a vessel, and is detachably mounted in a dispensing device comprising a drawing/discharging mechanism capable of adjusting the pressure in the container.

With the thirty second aspect, since the support for substances for detection is processed by using a dispensing device, various and diverse processes can be carried out by drawing or discharging a liquid to or from the container holding the support for substances for detection. Furthermore, complete processing including pre-processing, can be efficiently, consistently and automatically be performed, by using the dispensing device for dispensing a reagents etc. to each vessel, or for positioning a variety of substances for detection on the base member.

A thirty third aspect of the invention is a method of processing a support for substances for detection according to the thirtieth aspect, wherein at the installing step, the support for substances for detection according to any one of the first to the sixteenth aspects is installed so that the base member supported on the feed support section of the support for substances for detection can be fed, and at the transferring step, the substances for detection are transferred between processing regions by feeding only the base member in the direction of the length thereof with the support for substances for detection installed in the installing section.

With this aspect of the invention, the base member may be fed while expanding the integrated base member which is integrated in the integration supporting member.

With the thirty third aspect of the invention, only the base member of the support for substances for detection is fed in a direction of the length of the base member. Therefore, various processes can be carried out by only feeding the base member, thus facilitating processing and providing an overall compact processing apparatus.

A thirty fourth aspect of the invention is a method of processing a support for substances for detection according to the thirty third aspect, wherein at the transfer step, the base member of the support for substances for detection according to any one of the fifth to sixteenth aspects, is fed in a direction of the length of the base member, and the substances for detection are transferred between the processing regions, by connecting the feed support section to the feed mechanism and feeding.

With the thirty fourth aspect, only the support for substances for detection need be connected to the feed mechanism in order to feed the base member. Therefore the base member is not touched, and handling is easy.

A thirty fifth aspect of the invention is a method of processing a support for substances for detection according to the thirty third aspect, wherein at the transferring step, the supporting member of the support for substances for detection according to any one of the fifth to the sixteenth aspects, is transferred together with the installing section between the processing regions, and is rotated by connecting to the feed mechanism and only the base member is fed in the direction of the length, so that the substances for detection are transferred between the processing regions.

With the thirty fifth aspect of the invention, the base member is transferred by the inter-region transferring means and the feed mechanism. Therefore, in the case where a process having many steps is carried out, or the process needs a large apparatus or a large amount of space, the processes can be rationally and efficiently performed by separating the transferring step into two parts.

A thirty sixth aspect of the invention is a method of processing a support for substances for detection according to anyone of the thirtieth to the thirty-fifth aspects, wherein the processes in the processing regions are carried out in each vessel accommodating a variety of liquids.

A thirty seventh aspect of the invention is a method of processing a support for substances for detection according to any one of the thirtieth to the thirty-sixth aspects, wherein the processing step comprises a temperature control step for controlling temperature in the vessels.

A thirty eighth aspect of the invention is a method of processing a support for substances for detection according to any one of the thirtieth to the thirty-seventh aspects, wherein the processing step comprises a vibrating step for vibrating the vessel or the support for substances for detection.

A thirty ninth aspect of the invention is a method of processing a support for substances for detection according to any one of the thirtieth to the thirty eighth aspects, wherein the processing step comprises a drying step for drying the support for substances for detection to improve accuracy of detecting light emission.

A fortieth aspect of the invention is a method of processing a support for substances for detection according to any one of the thirtieth to the thirty-ninth aspects, wherein the processing step comprises a reacting step for reacting a suspension incorporating target substances with the substances for detection, and a detecting step for detecting a change such as light emission in the support for substances for detection, and further comprises an analyzing step for designating the relevant substances for detection on the basis of the detected location of the substances for detection on the base member, and analyzing a structure of a target substance on the basis of the structure of the substances for detection, A forty first aspect of the invention is a method of processing a support for substances for detection according to the fortieth aspect, wherein the detection step is carried out with the base member supported on the supporting member, in a state with the base member expanded, or in a state with the base member being fed.

With any one of the thirty sixth to the forty-first aspects, diverse and efficient processes can be carried out by using various apparatuses or carrying out various steps. Particularly, the reaction step can be sped up by vibrating the support for substances for detection itself or the vessel.

A forty second aspect of the invention is an apparatus for making a support for substances for detection comprising a dispensing device having one or more conduits and drawing/discharging means for adjusting a pressure in the conduits, a regeneration section for cleaning or exchanging the conduits, a vessel having a plurality of liquid containing portions accommodating suspensions incorporating a variety of substances for detection and into which the conduit can be inserted, a stage for arranging and stretching in parallel one or more base members according to any one of the first to sixteenth aspects of the invention which is to be dispensed, spotted, painted, or imprinted with liquid from said dispensing device, a displacement device which enables the movement of the conduits relative to the regeneration section, the vessels, the stage and the base member, and a control section for controlling the displacement device and the drawing/discharging means, and the control section controls in a manner that positions each suspension, on one or more base members, in substantially perpendicular directions to the length of the base member, along thin parallel lines, while keeping the lines from contact with neighboring lines, by repeating drawing, discharging, and displacement of each suspension incorporating the substances for detection, and cleaning or exchanging the conduits.

The reel wound by the base member can be made as follows:

At first, dispensation, spotting, painting, or imprinting of the suspension is carried out on a film, with parallel lines, by the apparatus. Thereafter, the film is rolled around a core in a direction perpendicular to the lines and integrated. Then, the rolled film is sliced in a direction perpendicular to the lines. Otherwise, the stretched base members are arranged on the stage in parallel. The film is then touched onto the base members with the parallel lines of the film substantially perpendicular to the length of the base members so that the suspensions are copied to the base members. The reel is then made as before.

A forty third aspect of the invention is an apparatus for making a support for substances for detection comprising a printing device having one or more conduits, one or more reservoirs accommodating suspensions incorporating various substances for detection and communicated with the conduits, and discharging means for discharging the suspension by adjusting a pressure within the conduits or reservoirs, a regeneration section for cleaning or exchanging the conduits and reservoirs, a stage for arranging and stretching one or more base members according to any one of the first to sixteenth aspects to be printed by the printing device, a displacement device which enables the movement of the conduits relative to the regeneration section, the vessels, the stage and the base member, and a control section for controlling the displacement device and the discharging means, wherein the control section controls in a manner that positions each suspension on one or more base members, in a substantially perpendicular direction to the length of the base members, along thin parallel lines, keeping each line from contact with the other lines, by repeating discharging, and displacement of the suspensions incorporating substances for detection, and cleaning or exchanging the conduits.

The reel wound by the base member can be made as follows:

At first, printing of the suspension is carried out on a film, in parallel lines, by the apparatus. Thereafter, the film is rolled around a core in a direction perpendicular to the lines and integrated. Then, the rolled film is sliced in a direction perpendicular to the lines. Otherwise, the base members are arranged and stretched on the stage in parallel. The film is then touched onto the base members with the parallel lines of the film substantially perpendicular to the length of the base members so that the suspensions are copied to the base members. The reel is then made as before.

A forty fourth aspect of the invention is an apparatus for making a support for substances for detection comprising one or more liquid retention tips such as a grooved needle, a pipe, a pen nib, or a linear imprinting part, a regeneration section for cleaning or exchanging the liquid retention tips, a vessel having a plurality of liquid containing portions accommodating suspensions incorporating a variety of substances for detection and into which the liquid retention tip can be inserted, a stage for arranging and stretching in parallel one or more base members according to any one of the first to the sixteenth aspects to be painted, written, stained, or imprinted by the liquid retention tips, a displacement device which enables the movement of the liquid retention tips relative to the regeneration section, the vessels, the base member, and the stage, and a control section for controlling the displacement device, wherein the control section controls in a manner that positions each suspension on one or more base members, in a substantially perpendicular direction to the length of the base member, along thin parallel lines, while keeping each line from contact with the other lines, by repeating holding and displacement of each suspension incorporating the substances for detection, and cleaning or exchanging the liquid retention tips.

The reel wound by the base member can be made as follows:

At first, painting, writing, staining, or imprinting of the suspension is performed on a film, with parallel lines, by the apparatus. Thereafter, the film is rolled around a core in a direction perpendicular to the lines and integrated. Then, the rolled film is sliced in a direction perpendicular to the lines. Otherwise, the base members are arranged and stretched on the stage in parallel. The film is touched onto the base members with the parallel lines of the film substantially perpendicular to the length of the base members so that the suspensions are copied to the base members. The reel is then made as before.

A forty fifth aspect of the invention is an apparatus for making a support for substances for detection according to any one of the forty-second to the forty-fourth aspects, wherein the control section controls the conduits or the liquid retention tips drawing, holding or storing a particular type of suspension, so as to position each suspension incorporating a substance for detection, along a parallel line while keeping each line from contact with the other lines, by repeating in order dispensing, painting, imprinting, staining, writing, or printing each type of suspension along lines in a direction perpendicular to the length of the base members, from a fixed location where one or more base members are mounted in parallel, and then controls to exchange or clean the conduits or liquid retention tips by the regeneration section, until all types of different suspensions are completed, for each position moved incrementally from the fixed location.

A forty sixth aspect of the invention is a method of making a support for substances for detection, comprising steps of: arranging and stretching one or more base members in parallel on a plane, positioning each substance for detection on the base members by dispensing, painting, staining, imprinting, writing or printing each suspension respectively incorporating a variety of substances for detection in many parallel thin lines, while keeping each line from contact with the other lines, and supporting the base members fixed with the substances for detection on a supporting member, wherein the fixed location of the substance for detection corresponds with the chemical structure thereof.

With this aspect of the invention, once a variety of substances for detection have been fixed to the base members, processes such as the slicing step as with the case of the film are not necessary.

A forty seventh aspect of the invention is a method of making a support for substances for detection according to the forty-sixth aspect, wherein the positioning step repeats in order; a step for drawing or holding a suspension incorporating a particular type of substance for detection by moving to and inserting a conduit or a liquid retention tip into a vessel accommodating the suspensions, a step for dispensing, painting, staining, imprinting, or writing the suspension in a direction substantially perpendicular to the length of the base member while displacing the conduit or the liquid retention tip from a predetermined location of the base members, and a regeneration step for cleaning or exchanging the conduit or liquid retention tip, so that each suspension incorporating substances for detection, is positioned in parallel lines while keeping each line from contacting the other lines.

A forty eighth aspect of the invention is a method of making a support for substances for detection according to the forty-sixth aspect, wherein the positioning step repeats in order; a step for printing a suspension incorporating a particular type of substance for detection by displacing a conduit communicated with a reservoir accommodating the suspension, while displacing the conduit from a predetermined location of the base members in a direction substantially perpendicular to the length of the base member, and a regeneration step for cleaning or exchanging the conduit and reservoirs, so that each suspension incorporating substance for detection, is positioned in parallel lines while keeping each line from contacting with the other lines.

With the forty second to the forty eighth aspect, with the plurality of thin expanded base members are arranged in parallel, each suspension incorporating substances for detection can surely be positioned in many parallel lines without generating cross contamination and without being intervened by human beings. Therefore, a reliable support for substances for detection can be provided in large quantities, at low cost.

Furthermore, with these aspects, lines of suspension incorporating substances for detection having appropriate width and concentration can be easily positioned by controlling the pressure in the conduits or displacement of the conduits or by adjusting the form of the conduit or liquid retention tips. Therefore, the aspects of the invention have diversity.

BRIEF DESCRIPTION OF THE DRAWINGS

FIG. 1 is a plan showing a support for substances for detection according to a first and second embodiment of the invention.

FIG. 2 is a plan showing a support for substances for detection of a third and fourth embodiment of the invention.

FIG. 8 is a plan showing a measuring step for the support for substances for detection of the eighth embodiment of the invention.

FIG. 15 is a plan showing a spacer member of a fifteenth embodiment of the invention.

DESCRIPTION OF THE PREFERRED EMBODIMENTS

Figure 3:
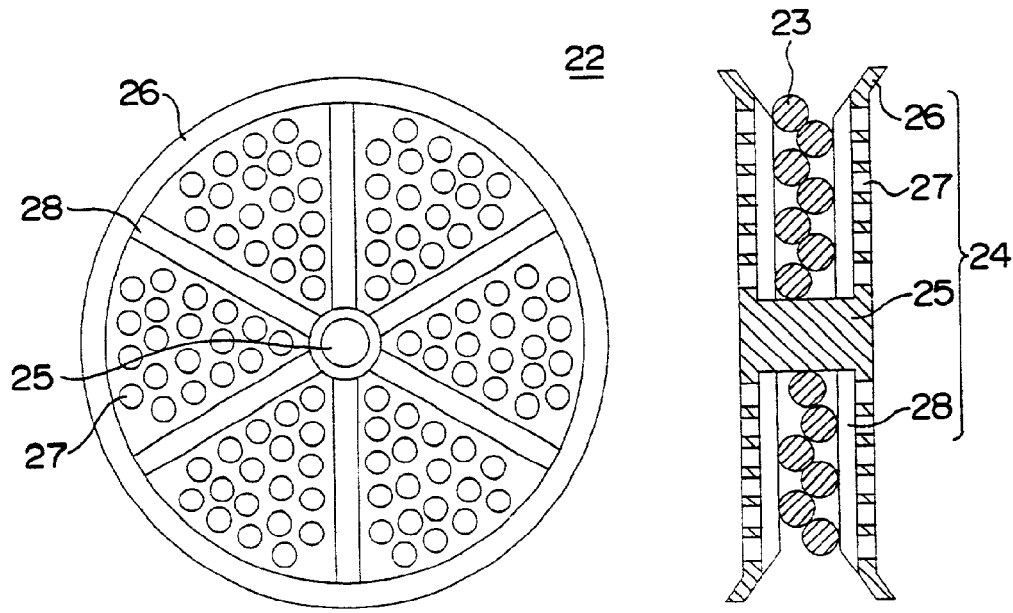
FIG. 3 is a plan showing a support for substances for detection of a fifth embodiment of the invention.

Embodiments of the invention are explained, on the basis of the drawings. These embodiments should not be interpreted as limiting the invention unless particularly specified.

FIGS. 1(a) (b) shows examples of a support for substances for detection of a first and second embodiment.

A support for substances for detection 10 according to a first embodiment of the invention as shown in FIG. 1(a) comprises a base member 11 that is formed to be long and slender and has pliability or flexibility, and a supporting member 12 on which the base member 11 is wound in a manner that enables expansion. On the base member 11, substances for detection, for example, oligonucleotides having a predetermined base sequence, are fixed side by side along the length of the base member. Each fixed location respectively corresponds with each base sequence thereof on the base member.

The base member 11 must be pre-processed on the surface thereof by coating with or being made of such material that can fix the substances for detection. A cross section of the base member 11 is substantially circular, as a circle or ellipse. Plural angular projections 11a are mounted on the outer periphery along the circumference at predetermined intervals.

The base member 11 is made of, for example, a synthetic resin such as nylon, polyethylene, or polyester. The oligonucleotide is fixed in each division partitioned by the angular projections 11a. The angular projections 11a can prevent the base member 11 from adhering to itself or adhering to the other members, and can generate space in such a manner that a liquid can flow around the base member 11.

Therefore, encounter rate between, such substances for reaction such as target substances suspended in a liquid and substances for detection fixed to the base member, can be improved, and reaction or combination between them can be encouraged. Furthermore, since a liquid can spread around all the substances for detection and does not contact with only a part of the substances, reliable analysis or examination can be performed.

Furthermore, the supporting member is a reel 12 shown in FIG. 1(a). The reel 12 comprises a core 13 formed to be cylindrical, and two guide frames 14 formed to be disk-like and mounted on the opposite ends of the core 13 with axes of the core 13 and the guide frames 14 coinciding. In this example, the predetermined spacing is a width (length of cylinder) about which a maximum of three rows of base member 11 can be wound. Furthermore, a plurality of holes 15 are formed in the surface of the guide frames 14. A liquid can pass through the holes 15. It is preferable that the base member 11 is made of a transparent material to ensure that radiation is captured.

With this example, as shown in FIG. 1(a), the base member 11 is wound and arranged in a state that the first layer has three lines, the second layer has two lines, and so on. Therefore, the base member 11 is gathered closely together, and the degree of integration can be improved. Since the base member can be gathered into a compact size, processing with a lesser amount of liquid can be carried out.

The diameter of the core 13 of the reel 12 is for example, 5 mm and the diameter of the base member 11 is for example, 0.05 mm, and the length of the base member 11 is for example, 2000 mm. For example, 1000 types of substances for detection are fixed in a width of for example 1 mm, and at intervals of for example, 0.6 mm. For example, 30 rows of base member 11 are wound around the core 13, at intervals of for example, 0.05 mm. In this case, the necessary width of the core 13 is, about (0.05+0.05)×30=3 mm.

In this case, whole area of the surface of the base member 11 is:

$2\pi \times 0.025 \times 2000 =$ about 314 mm$^2$.

The painting area of the substances for detection is $2\pi \times 0.025 \times 1 \times 1000$ (locations)=about 157 mm$^2$.

The density of the positioned substances for detection is:

1000(locations)/314 mm$^2$=about 300/100 mm$^2$.

Furthermore, since the circumference of the core 13 is:

$2\pi \times 2.5 =$about 15.7 mm.

The length of the path around the reel 12 that is wound with 30 rows is:

15.7×30=about 471 mm.

Therefore, the base member is overlapped on the core 13:

2000 mm/471=about 4.24 overlapping turns.

Hence, the necessary diameter of the reel 12 is:

5+(0.05+0.05)×4.24=about 5.42 mm.

FIG. 1(b) shows a support for substances for detection 16 of the second embodiment. The support for substances for detection 16 is different from the support for substances for detection 10 shown in FIG. 1(a), in that a reel 17 having a core 18 whose width (length of the cylinder) is wide enough for the base member 11 to be wound thereon in one row is used. Consequently, the base member 11 can be wounded on the reel 17, without overlapping in the direction of width. In this case, when for example the reel 17 is made of a transparent body or is formed to have a plurality of apertures or openings, light emission can be detected with the base member wound on the reel 17.

In regard to the reel 17, an integrated state and expanded state will be explained giving specific numerical value examples.

The diameter of the core 18 of the reel 17 is for example, 3 mm, and the base member 11 is the same as for the case of the reel 12. Only one row of base member 11 is wound on the reel 17. In this case, the necessary width of the core 18 is 0.05 mm. The necessary diameter of the reel 17 in which the core is mounted is about 11.80 mm, according to computer calculations. If the diameter of the core 18 is about 5 mm, the necessary diameter of the reel 17 is about 12.80 mm.

In either case, the necessary diameter of the reel 17 is for example, of the order of about 1 mm~the order of 1 cm. The diameter of the base members is for example of the order of about 0.001 m–0.1 cm. The interval of positioned substances for detection is for example of the order of about 0.01 mm–1 mm. The length of the base member is for example of the order of about 1 m.

FIG. 2(a) shows a support for substances for detection 19 of a third embodiment. The support 19 of this embodiment, uses the same reel 12 shown in FIG. 1(a). But the support 19 is different from the one shown in FIG. 1(a), in that the base member 11 is loosely wound on the reel 12 without alignment.

Hence, since sufficient space can surely be obtained around the base member, a suspension to be reacted can spread around the base member, and efficiency of reaction and encounter rate of the substances for detection can be uniformly improved.

FIG. 2(b) shows a support for substances for detection 20 of a fourth embodiment. The support for substances for detection 20 of this embodiment is integrated by using the same reel 12 as the one shown in FIGS. 1(a) and 2(a), and winding a base member 21 different from the base member 11 loosely, without alignment. The base member 21 is formed to be circular or substantially circular in a cross section thereof. On the outside surface of the base member 21, projections 21a are radially projected, for instance, in six directions separated by a predetermined angle to each other and arranged along the length thereof.

With this example, since sufficient space can be obtained around the base member 21 or between the base member and the guide frames 14, a liquid to be reacted can uniformly go around each substance for detection, and encounter rate between substances to be reacted can be further improved.

Figure 4:
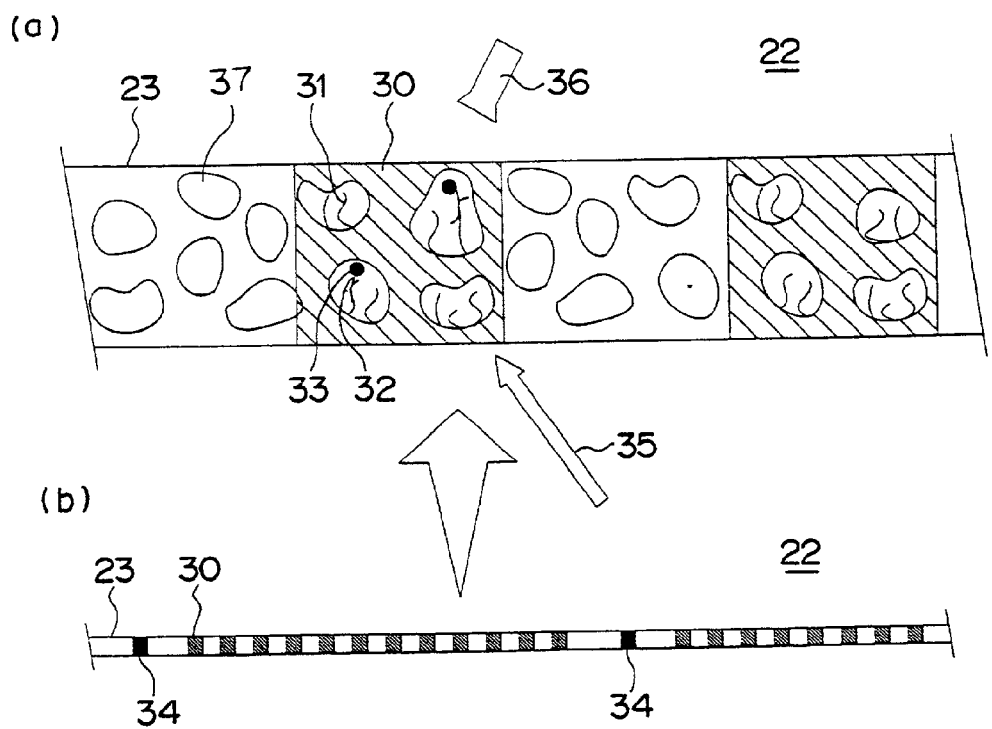
FIG. 4 is a plan showing a base member of a support for substances for detection of the fifth embodiment of the invention.

FIG. 3 shows a support for substances for detection 22 of a fifth embodiment. This support for substances for detection 22 comprises a base member 23 that is flexible and has a thin and slender shape such as thread or string of circular cross section, and a reel 24 on which the base member 23 is wound in such a manner that enables or prevents expansion and which is used as a supporting member. As shown in FIG. 4, for example, oligonucleotides having a particular base sequence, serving as substances for detection, are fixed by arranging along the length of the base member. Thus each fixed location and each base sequence corresponding the chemical structure, are respectively related.

As shown in FIG. 3, this support for substances for detection 22 comprises a reel 24 that constitutes the supporting member, having a core 25 formed to be cylindrical, and two guide frames 26 being permeable and mounted on the opposite ends of the core 25.

Furthermore, a plurality of holes 27 are formed in the surface of the guide frame 26. A liquid can pass through the holes 27. Six projections 28, serving as spacer members, are projected inwardly from each guide frame 26 and are radially extended along each guide frame 26, respectively, in order to prevent the base member 23 from sticking to the guide frames 26. These projections 28 on the opposite guide frames 23 are mounted in such a manner that are opposed face to face or alternatively.

Due to these projections 28, the base member 23 aligned with 3 rows originally is pressed inwardly so as to be away from the guide frames 26, resulting in cramming into 1.5 rows. Thus the projections 28 prevent the base member 23 from aligning with and adhering to the guide frames 26, and form a space between the base member 23 and the guide frames 26, to allow a liquid to flow through the space. Hence the encounter rate between the substances for detection and a liquid to be reacted can be improved.

FIGS. 4(a) and 4(b) show, in detail an enlarged base member 23 constituting the support for substances for detection of a fifth embodiment. As shown in FIG. 4(a), the base member 23 is made of porous material, has a plurality of minute pores 37, and can be impregnated by a liquid. In the base member 23, fixing regions 30 where particular types of substances for detection are respectively fixed, are arranged at predetermined intervals.

As the substances for detection 31, for example, oligo-nucleotides having particular types of base sequence are used. FIG. 4 shows an example of the case when gene substances 32 such as DNA fragments, used as a target substance having an unknown base sequence to be determined, being marked by a luminous substance 33 such as a fluorescent substance, are combined by hybridization with substances for detection 31 fixed at the region 30.

In FIG. 4(b), reference numerals 34 denote marks provided on the base member 23 at predetermined intervals, in order to indicate the standard position thereon, being made of a luminous substance such as a fluorescent substance.

Excitation light, from for example alight source, is irradiated onto the base member 23 combined with the target substance, and radiation from the luminous substance 33 and the mark 34 is received by a receiving means 36. The region 30 on the base member 23 is specified from a location of radiation. From the location of the region 30 on the base member 23, the base sequence of the oligonucleotide used as the substance for detection fixed on the region 30 where the target substance is combined, can be determined. By determining the base sequence, the base sequence of the target substance can be determined.

Figure 5:
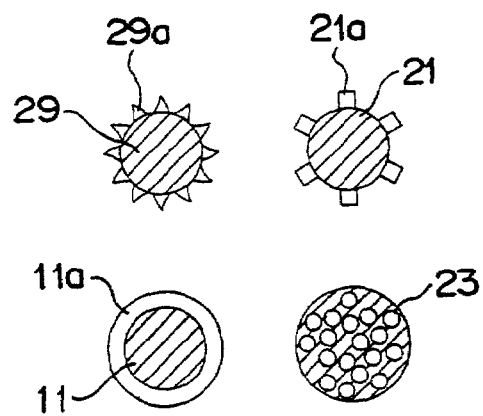
FIG. 5 is a sectional plan view of examples of base members of embodiments of the invention.

FIG. 5 shows examples of various cross sections of base members 11, 23, 21 and 29 which include the base members that have already been explained. Reference numeral 29a denotes a projection provided on an outer peripheral surface of the base member.

FIGS. 6(a) and (b) show supports for substances for detection 40, 50 of sixth and seventh embodiments. The support for substances for detection 40 shown in FIG. 6(a), comprises a cassette-like supporting member. The support for substances for detection 40 comprises a casing used as a frame body, and an arm 45 extending outwardly from the casing 44. In the casing 44, two reels 41, 42 on which the base member 43 can be wound are fitted to the casing 44, in a manner that enables rotation. At the end of the arm 45, a roller 46 is mounted in a manner that enables rotation.

The base member 43 is wound on the reels 41, 42 in a manner allowing winding up and unwinding, and is routed around the roller 46, between the reel 41 and the reel 42. A feed mechanism (not shown) is mounted to drive the reel 41 and the reel 42 to rotate alternately so that the base member 43 is fed.

A plurality of types of substances for detection are positioned and fixed on the base member 43, along the length thereof at predetermined intervals. Inspection, examination or analysis by using the support for substances for detection 40 having the cassette like supporting member, can be carried out by inserting the roller 46 mounted at the end of the arm 45 into a vessel 48 accommodating a suspension incorporating a predetermined target substance. The regions on which the substances for detection are fixed on the base member, are transferred from the one reel to the other reel by rotating the reel 41 or the reel 42.

The reels 41, 42 and the roller 46 correspond to the feed support section for feeding the base member 43, and constitute the supporting member together with the frame body.

In order to process the support for substances for detection 40 of the embodiment, at first, this support for substances for detection 40 is installed in an installing section (not shown). The support for substances for detection 40 is then transferred to the processing region where the vessel 48 holding a suspension incorporating target substances is set up, and the roller 46 mounted on the arm is inserted into the vessel 48.

Thereafter, the base member 43 integrated on the reel 41 is pulled by rotating the reel 42, and is fed along the feed path so that the whole of the base member for detection can contact and react with the suspension incorporating the target substance uniformly.

Next, the support for substances for detection 40 is moved to a vessel holding a cleaning liquid of the next processing region while installed in the installing section. Thereafter, the base members 43 is fed through the cleaning liquid, by rotating the reel 41 in the direction opposite to that in the processing region.

Furthermore, with the support for substances for detection 40 installed in the installing section, the support for substances for detection is moved to the subsequent processing regions, and cleaning, drying or detecting is carried out by rotating in the direction opposite to that in the preceding processing region.

Detection is performed by irradiating excitation light from the light source onto the base member 43 while feeding the base member 43 along the feed path and receiving the light emission with the receiving section, in order to detect the substance for detection combined with the target substance marked by a fluorescent substance. If each end of the base member 43 is respectively connected to each reel, the base member 43 will not come.

The support for substances for detection 50 shown in FIG. 6(b) of the seventh embodiment, comprises a cassette-like supporting member. The support for substances for detection 50 comprises a casing 54 used as the frame body, and an arm 55 extending outwardly from the casing 54. A drum 51 capable of rotating is fitted in the casing 54.

A roller 56 is mounted on the end of the arm 55. The base member 53 is wound along the bottom of a thread formed on the outer surface of the drum 51, and can move along a closed loop pathway routed from the drum 51, around the roller 56 and back to the drum 51.

Plural types of substances for detection are fixed side by side along the length thereof at predetermined intervals. The drum 51 and the roller 56 correspond to the feed support section, and constitute the supporting member together with the frame body.

Figure 6:
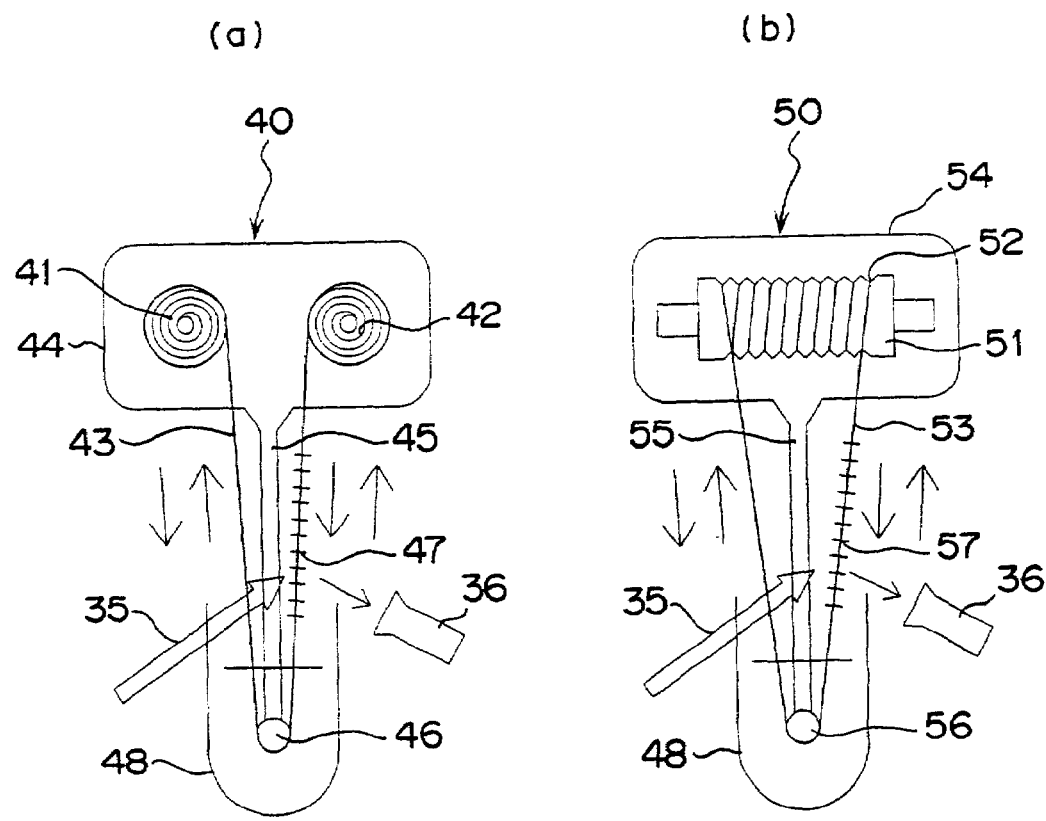
FIG. 6 is a plan showing a support for substances for detection of a sixth and seventh embodiment of the invention.

Since the process of the support for substances for detection 50 having a cassette-like supporting member is substantially the same as for the case of the support for substances for detection 40 explained on the basis of FIG. 6(*a*), explanation thereof is omitted.

Figure 7:
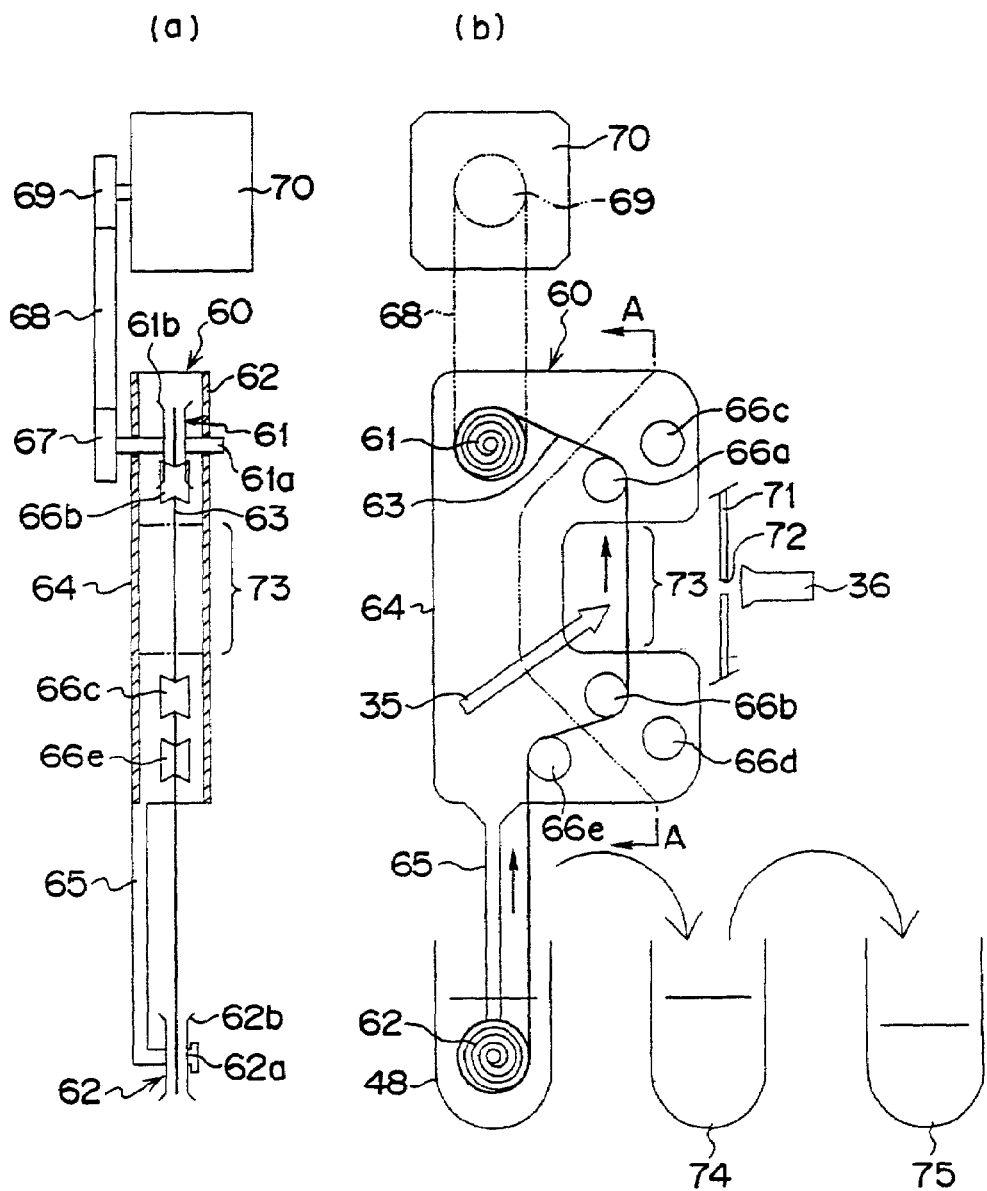
FIG. 7 is a plan showing a support for substances for detection of an eighth embodiment of the invention.

FIG. 7 shows a support for substances for detection 60 of an eighth embodiment.

This support for substances for detection 60 comprises a take-up reel 61 and supply reel 62. A base member 63 is routed around rollers 66*a*, 66*b* and 66*e*, between the take up reel 61 and the supply reel 62.

Furthermore, the support for substances for detection 60 comprises a casing 64 used as the frame body and a thin arm 65 extending from the casing 64. The take-up reel 62 and rollers 66*a*, 66*b*, 66*c*, 66*d* are rotatably mounted within the casing 64. The supply reel 62 is rotatably mounted on the end of the arm 65 in such a manner that enables insertion into the vessel 48 etc. The take-up reel 61, the supply reel 62 and the rollers 66*a*, 66*b*, 66*c* and 66*d* correspond to the feed support section, and constitute a supply member, together with the frame body.

As shown in FIG. 7(*a*), the take-up reel 61 and the supply reel 62 respectively comprise cylindrical cores 61*a*, 62*a*, and two guide frames 61*b*, 62*b* through which liquid can pass, respectively mounted on the opposite ends of the cores 61*a*, 62*a*, at predetermined spacing.

The core 61*a* of the take-up reel 61 can connect to a gear 67 provided outside thereof, on the same axis. This gear 67 is mechanically connected to a gear 69 of a motor 70, through a timing belt 68. The gear 67, the timing belt 68, the gear 69 and the motor 70 constitute the feed mechanism.

Further, the pathway of the base member 63 between the roller 66*a* and the roller 66*b*, and outside of the casing 64, is used as a detection region 73. The substances fixed on the base member 63 are detected by obtaining light from a specified position in the detection region 73. A screen 71 provided with a slit 72 is mounted in such a manner that the detection region 73 is covered except the specified position.

On the side of the screen 71 opposite to the detection region 73, a receiving section 36 is mounted. In order to examine and analyze using the support for substances for detection 60 having this cassette like supporting member, at first, the supply reel 62 wound by the base member 63 is rotatably mounted on the lower end of the arm 65. The end of the base member 63 is then fixed to an empty take-up reel 61. At this stage, the substances for detection have already been fixed to the region of the base member wound on the supply reel 62.

The reaction between the target substance and the substances for detection is carried out by inserting the lower end of the arm 65 into the vessel 48 holding a suspension incorporating the target substance marked by a fluorescent substance.

In this case, it is preferable to vibrate the vessel or the support for substances for detection 60.

After a predetermined time passes, the supply reel 62 mounted on the lower end of the arm 65, is taken out from the vessel 48, and is transferred to and inserted into a vessel 74 holding a first cleaning liquid. After inserting, unnecessary suspension stuck to the supply reel 62 is removed by vibrating the vessel 74.

Thereafter, the supply reel 62 is again taken out from the vessel 74, and is inserted into a vessel 75 holding a second cleaning liquid as a precaution, the vessel 75 is vibrated, to get rid of contaminants stuck to the supply reel 62.

With the supply reel 62 soaked in the clearing liquid, or with the supply reel 62 taken out from the vessel, or after drying, the base member 63 is fed from the supply reel 62 to the take-up reel 61, by rotating the take-up reel 61 with the motor 70.

In this case, it is preferable that the roller 66*b* is made of a material that can absorb water when the base member passes over the roller 66*b*. When the base member 63 is fed through the detection region 73, the excitation light 35 from the radiation source is irradiated, and light emission at predetermined locations is received by the receiving means. From the result of the received light emission, the structure of the target substance can be analyzed. Incidentally, the function of the rollers 66*c*, 66*d* will be explained below, on the basis of FIG. 13.

FIG. 8 shows the case when many supports for substances for detection 60 of an eighth embodiment are arranged in a row, a process of the supports for substances for detection is carried out, and then detection of light emission is carried out at the same time. In this case, a light source irradiates the excitation light 35 across the row of the casings of the supports for substances for detection into the detection regions 73, all together. Therefore, in each support for substances for detection 60, light emission can be detected or measured simultaneously, and the process and the measurement can be efficiently be carried out.

Figure 9:
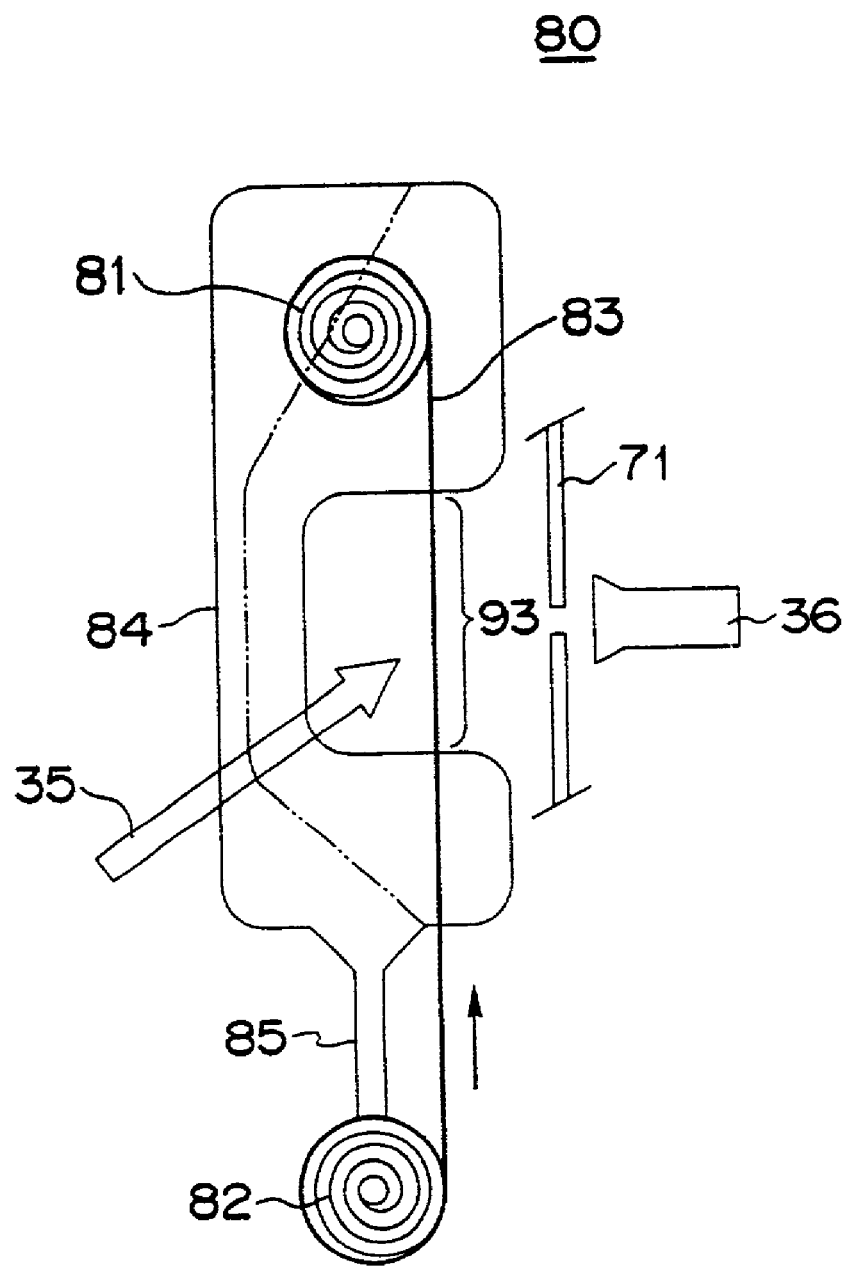
FIG. 9 is a plan showing a support for substances for detection of a ninth embodiment of the invention.

FIG. 9 shows a support for substances for detection 80 of a ninth embodiment. This support for substances for detection 80 comprises a take-up reel 81 and a supply reel 82 constituting a feed support section, which can respectively wind up and unwind the base member 83. The base member 83 is routed directly between the take-up reel 81 and the supply reel 82, without other rollers. Further, the support for substances for detection 80 comprises a casing 84 used as the frame body and a thin arm 85 extending from the casing 84. The take-up reel 81 is rotatably mounted in the casing 84. The supply reel 82 rotatably is mounted on the lower end of the arm 85 in such a manner that enables insertion into the vessels etc. The reels 81, 82 correspond to the feed support section, and together with the frame body constitute a supporting member.

Since the support for substances for detection 80 of the embodiment has a structure such that the base member 83 can be fed without intervening rollers, the support for substances for detection 80 has a simpler structure than the ones having rollers, and can reliably prevent the base member 83 from being rubbed or generating cross contamination.

Figure 10:
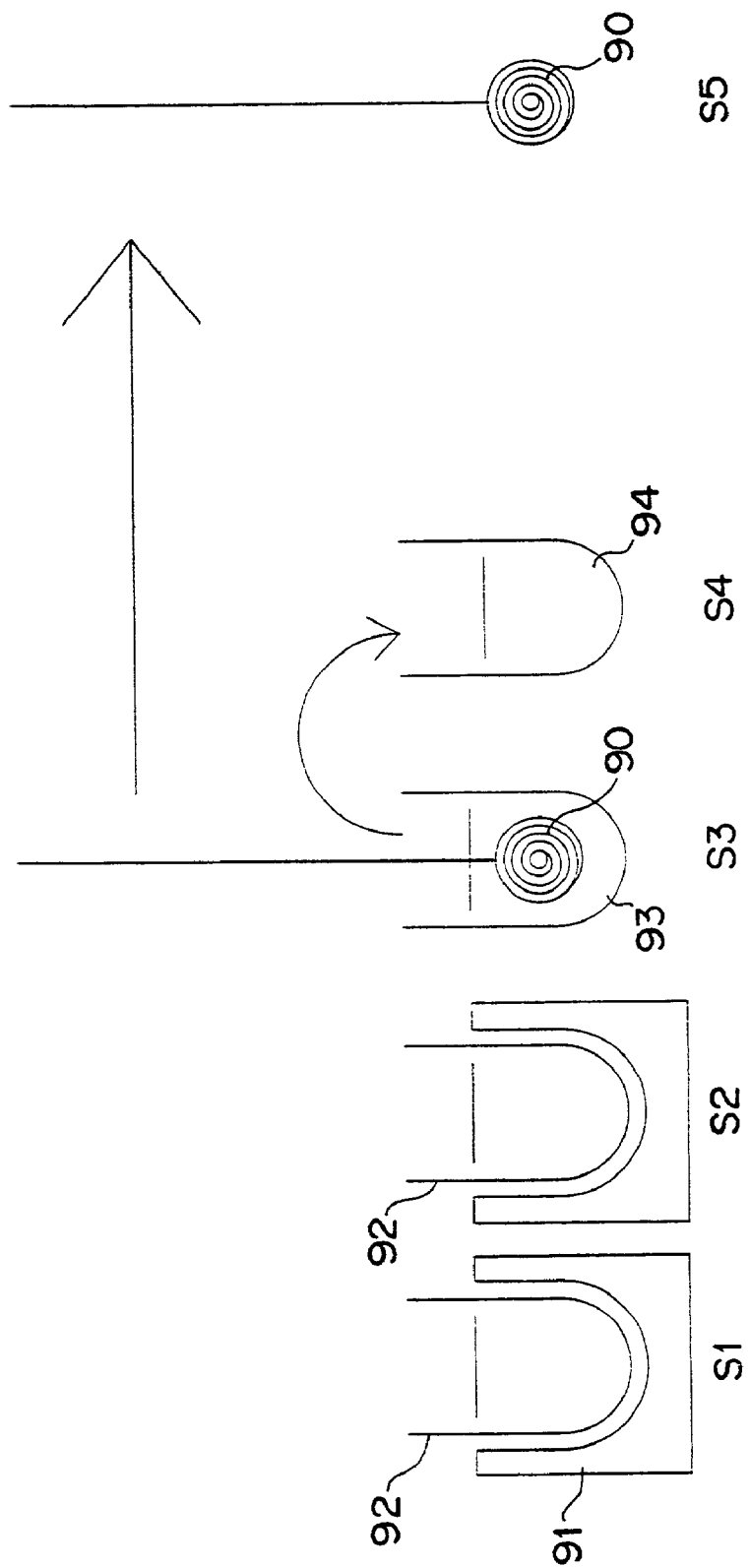
FIG. 10 is a plan showing a method of processing a support for substances for detection of a tenth embodiment of the invention.

FIG. 10 shows an example of a method of processing a support for substances for detection of a tenth embodiment.

The method of processing the support for substances for detection is explained by giving an example of process for determining an unknown base sequence of DNA fragments used as a target substance. The method of the embodiment has the characteristics that the support for substances for detection 90 is transferred while installed on the installing section (not shown), without being expanded.

As shown in FIG. 10, at step S1, a suspension incorporating target substances marked by fluorescent substances etc. is mixed with a predetermined reagent to obtain a probe solution. The probe solution is pre-heated to about 95° C. for a few minutes, in a thermostatic tub 91 where a Peltier effect device is mounted. Thereafter, a direction of the current in the Peltier effect device is changed, and the probe solution is cooled to for example a normal temperature or, if necessary, a temperature different from the normal temperature and adjusted so as to facilitate hybridization.

In order to determine unknown base sequence of DNA fragments, it is needless to say that in addition to hybridization processes such as polymerization of DNA fragments, and denaturation of DNA fragments are necessary as a prerequisite.

At step S2, the integrated support for substances for detection 90 is transferred and inserted into a vessel 92 accommodating the probe solution. Thereafter, the vessel 92 is transferred to the thermostatic tub 91 and for instance, is kept at for example, a normal temperature or, if necessary, a temperature different from the normal temperature, for about a few minutes to a few hours in order to carry out incubation and reaction.

At step S3, after completing reaction, the support for substances for detection 90 is transferred to and inserted into a vessel 93 accommodating a first cleaning liquid, and is vibrated and cleaned at room temperature so that remnants of the probe solution suspending target substances are removed.

At step S4, after the first cleaning, the support for substances for detection 90 is transferred to and inserted into a vessel 94 accommodating a new second cleaning liquid, and is cleaned again by vibrating the vessel, and, remnants of the probe solution are removed.

At step S5, after drying the support for substances for detection 90 by blowing dry air thereon, the light emission is detected, with the support 90 being integrated or expanded.

Figure 11:
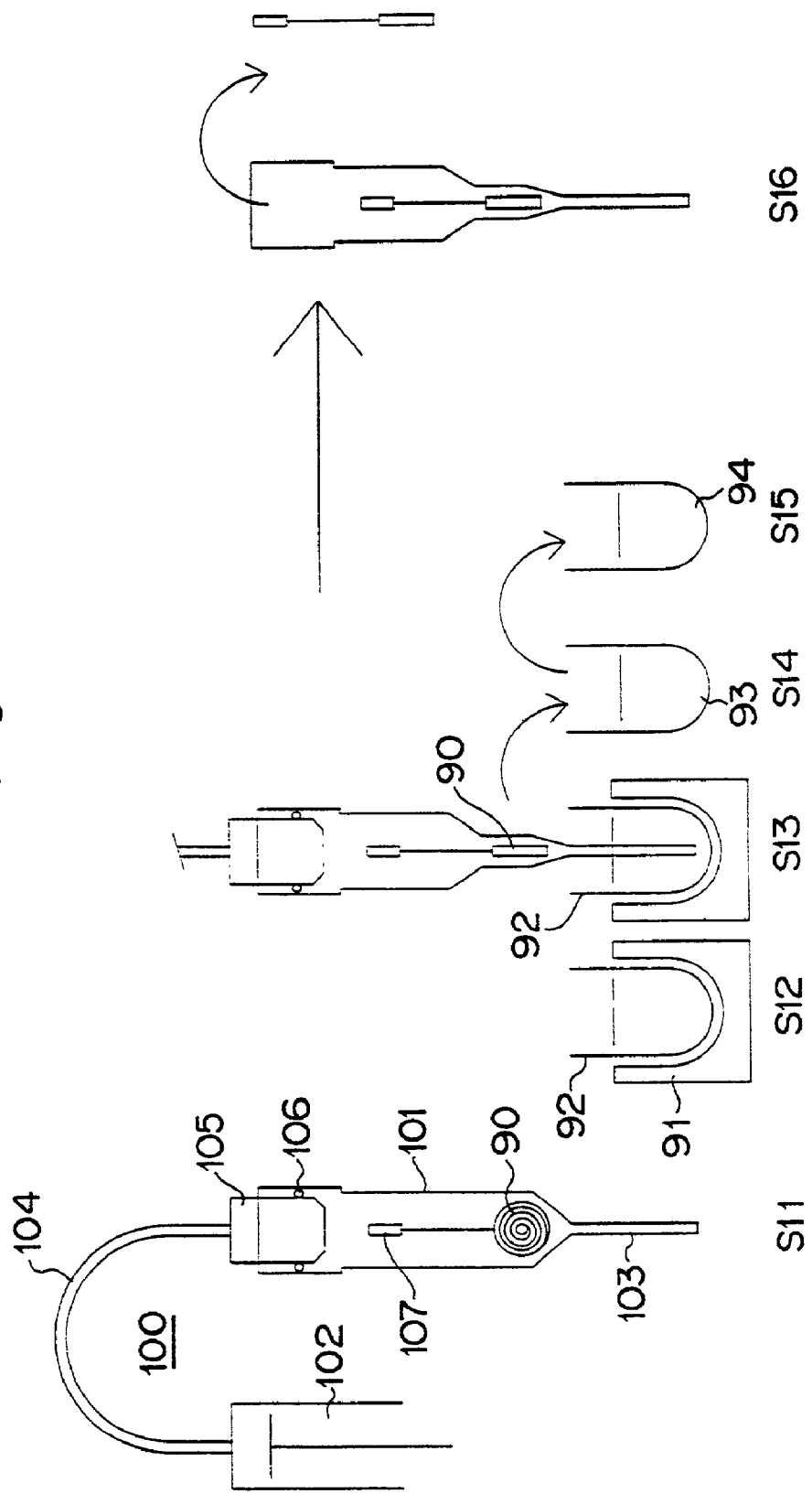
FIG. 11 is a plan showing an apparatus for processing a support for substances for detection and a method of processing a support for substances for detection of an eleventh embodiment of the invention.

FIG. 11 illustrates an apparatus and method for processing a support for substances for detection of an eleventh embodiment, taking as an example a process for determining an unknown base sequence of DNA fragments used as the target substance.

As shown in FIG. 11, with the embodiment, a dispensing device 100 is used as the apparatus for processing the support for substances for detection, and the support for substances for detection 90 is installed into the installing section of the dispensing device, and is transferred together with the installing section. The dispensing device 100 comprises a reservoir section 101 serving as a container, for storing a liquid and capable of accommodating the support for substances for detection 90, a drawing/discharging mechanism 102 such as a cylinder for adjusting a pressure within the reservoir section 101 to draw in and discharge a liquid, and a small diameter section 103 communicating with the reservoir section 101 and capable of being inserted into a vessel in a processing region set up outside of the dispensing device.

The reservoir section 101 is fitted to a nozzle 105 communicating through a pipe 104 with the drawing/discharging mechanism in such a manner that enables dismounting. A sealing member such as an O-ring, is mounted in the nozzle 105, to prevent liquid leakage.

Within the reservoir section 101, the support for substances for detection 90 is attached to an installing section 107 provided on an inner wall of the reservoir section 101.

Though not shown in figure, this apparatus comprises, a transfer means for transferring the reservoir section 101 and the small diameter section 103, and a control section for controlling the transfer means and the drawing/discharging mechanism 102.

This control section comprises an information processing device having an inputting section for instructing an operation or inputting data by an operator, an output section for displaying or outputting a result of the operation and contents of the instruction or data to the operator, a data storing device, and an arithmetic unit such as a CPU for analyzing the instructions of the operation, instructing each unit, displaying the results of the operation and analyzing.

With the method of processing the support for substances for detection of the eleventh embodiment, at step S11, the support for substances for detection 90 is installed into the reservoir section 101 of the dispensing device 100. The reservoir section 101 is then fitted to the nozzle 105.

At step S12, after pre-heating the vessel 92 accommodating the probe solution in which a suspension incorporating target substances marked by fluorescent subjects is mixed with predetermined reagents, by means of the thermostatic tub 91 having the Peltier effect device, to a temperature of about 95° C. for a few minutes, the suspension is adjusted by reversing the direction of the current in the Peltier effect device to cool to for example a normal temperature or, if necessary, a temperature different from the normal temperature.

At step S13, the support for substances for detection 90 is transferred together with the reservoir section 101. The small diameter section 103 of the dispensing device 100 is inserted into the vessel 92. The vessel 92 is kept at for example a normal temperature or, if necessary, a temperature different from the normal temperature, for about a few minutes to a few hours, by the thermostatic tub 91 so that the support is incubated and reacted. In this case, the dispensing device 100 is repetitively operated at regular intervals to draw a liquid into the vessel 92 and discharge the liquid, so that the support for substances for detection 90 within the reservoir 101 can contact with the liquid at the aforesaid temperature.

At step S14, after completing the reaction, the support for substances for detection 90 is transferred to a vessel 93 accommodating a first cleaning liquid at room temperature, together with the reservoir section 101, and the small diameter section 103 of the dispensing device 100 is inserted into the vessel 93. Then the support 90 is cleaned with repetitively drawing in and discharging the cleaning liquid with the dispensing device 100, so that remnants of the probe solution suspending the target substance can be removed.

At step S15, after the first cleaning, the support 90 is transferred to a vessel 94 accommodating a new second cleaning liquid together with the reservoir section 101. The small diameter section 103 is inserted into the vessel 94. Then the support for substances for detection 90 is cleaned by repetitively drawing in and discharging the cleaning liquid by the dispensing device 100, so that remnants of the probe solution can be further removed.

At step S16, the support for substances for detection 90 for which cleaning is completed, is removed from the reservoir section 101 to outside. Then the support is dried by blowing with dry air, the dried support 90 is expanded, and optical detection is carried out.

Figure 12:
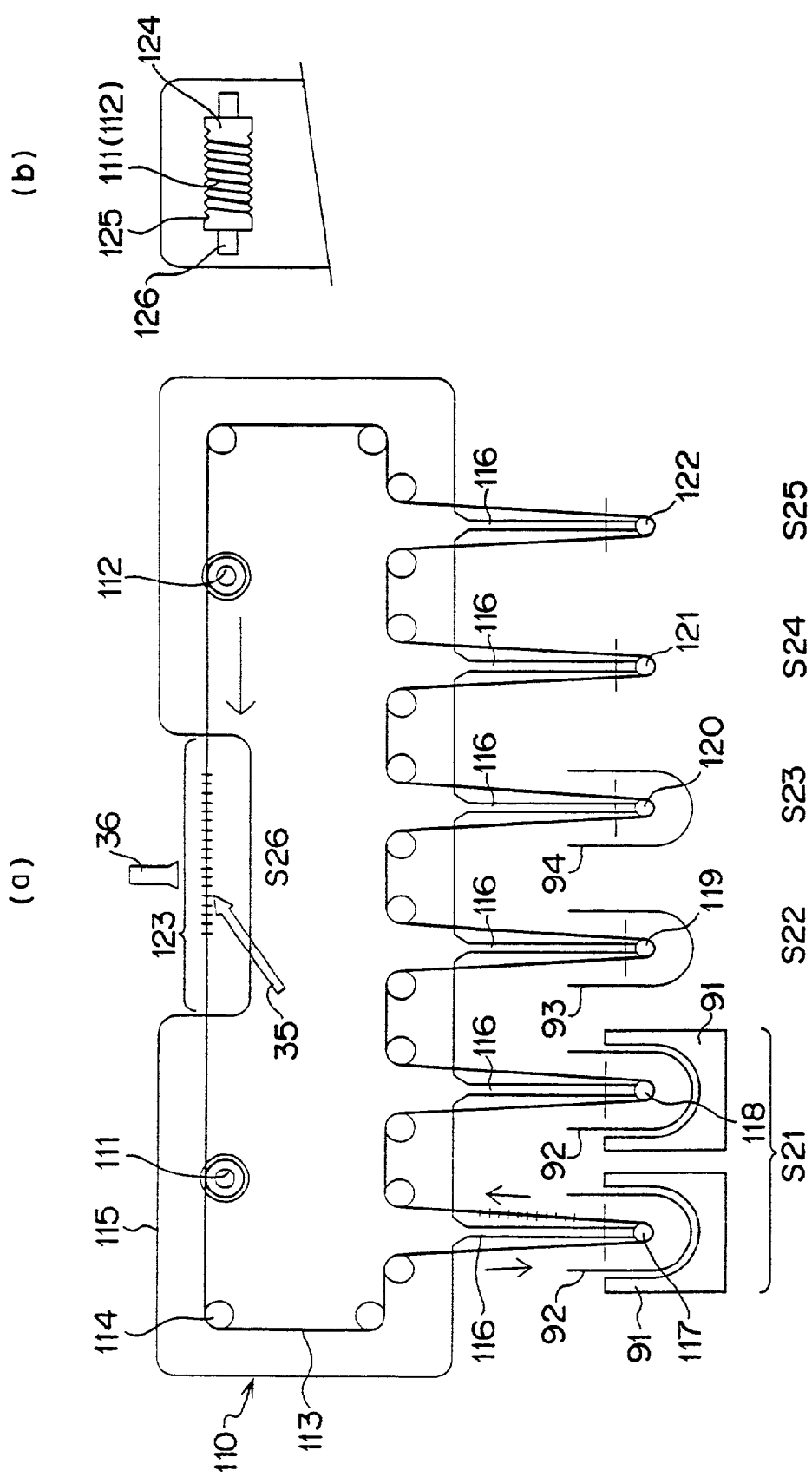
FIG. 12 is a plan showing an apparatus for processing a support for substances for detection and a method of processing a support for substances for detection of a twelfth embodiment of the invention.

Next, the support for substances for detection 110 of a twelfth embodiment and the method of processing the support are explained on the basis of FIG. 12.

The support for substances for detection 110 of the twelfth embodiment, comprises two drums 111, 112 capable of unwinding and winding up a base member 113. The base member 113 is formed as a thin string, and is wound on the drum 111 and drum 112, and looped with a routed feed path around sixteen rollers 114 and six rollers 117~122.

Further, the support for substances for detection 110 comprises a casing 115 used as the frame body, and six thin arms 116 extending downwardly from the casing 115.

Drums 111, 112 and the sixteen rollers 114 are rotatably mounted within the casing. The six rollers 117~122 are rotatably mounted at the lower end of the arms 116. The lower ends of the arms 116 are formed to be small enough to be able to be inserted into the vessels 92, 92, 93 and 94. The rollers 117~120 mounted at the lower end of the arms 116 are inserted into the vessels 92, 92, 93 and 94 respectively, and the rollers 121, 122 are exposed in the air.

Further, many types of substances for detection are positioned along the length of the base member 113 at regular intervals. A part of the running pathway of the base member 113 is set up in such a manner that passes through a detection region 123 which is mounted outside of the casing 115.

As shown in FIG. 12(b), the drum 111 (or drum 112) comprises a drum-like core 124, a rotational shaft 126 concentric with the core 124, and a recessed thread 125 formed in the outer surface of the core 124, and the base member 113 is wound along the thread 125.

The drums 111, 112 and rollers 117~122 correspond to the feed support section, and constitute the supporting member together with the frame body. Though not shown in the figure, this apparatus comprises a feed mechanism for rotating the drum 111 or the drum 112 to feed the base member 113 of the support for substances for detection 100, by loading the support for substances for detection 110 thereinto, and a control section for controlling the feed mechanism.

Next, the method of processing the support for substances for detection of the twelfth embodiment using the support for substances for detection 110 will be explained.

At step S21, after heating the vessel 92 accommodating the probe solution in which a suspension incorporating the target substances marked by the fluorescent substances is mixed with a reagent, to a temperature of about 95° C. for a few minutes by the thermostatic tub 91 having the Peltier effect device, the probe solution is adjusted by reversing the direction of current in the Peltier effect device and cooled to for example a normal temperature or, if necessary, a temperature different from the normal temperature to facilitate hybridization in the solution.

Next, the vessel 92 is held at for example a normal temperature or, if necessary, a temperature different from the normal temperature by the thermostatic tub 91. In this state, incubation and reaction of the portion of the base member 113 passing around the rollers 117, 118 is carried out portion by portion for about a few minutes to a few hours. By driving the drum 111, 112 so as to maintain the speed, the substances for detection fixed on the base member 113, are moved along.

At step S22, at the maintained speed, the portion of the base member 113 for which the reaction is completed passes around the roller 119 which is inserted into the vessel 93 accommodating the first cleaning liquid. On that occasion, remnants of the probe solution suspending the target substance are removed and the portion of the base member 113 is cleaned by vibrating the vessel.

At step S23, at the maintained speed, the portion of the base member 113 for which the first cleaning is completed is passed around the roller 120 which is inserted into the vessel 94 accommodating the second cleaning liquid and this passes therethrough. On that occasion, the portion of the base member 113 is cleaned by vibrating the vessel, and remnants of the probe solution suspending the target substance that could not be cleaned out at the first cleaning are removed.

At step S24, at the maintained speed, when the portion of the base member 113 for which the second cleaning is completed passes around the roller 121, that portion is dried by blowing with dry air.

At step S25, at the maintained speed, the portion of the base member 113 dried at the previous step, is further blown with dry air, so that water which could not be removed by the first dry, is removed completely.

At step S26, at the maintained speed, when the portion of the base member 113 for which the drying is completed, passes through the detection region 123, the excitation light 35 is applied to that portion, and light emission is received by the receiving section 36.

With the method of the embodiment, since the support for substances for detection 110 per se needs not be moved and only the base member 113 is fed by rotating the drums 111, 112, the structure of the transfer means can be simplified, and the apparatus can be downsized. The method of this embodiment is particularly effective in the immunoreactions.

Figure 13:
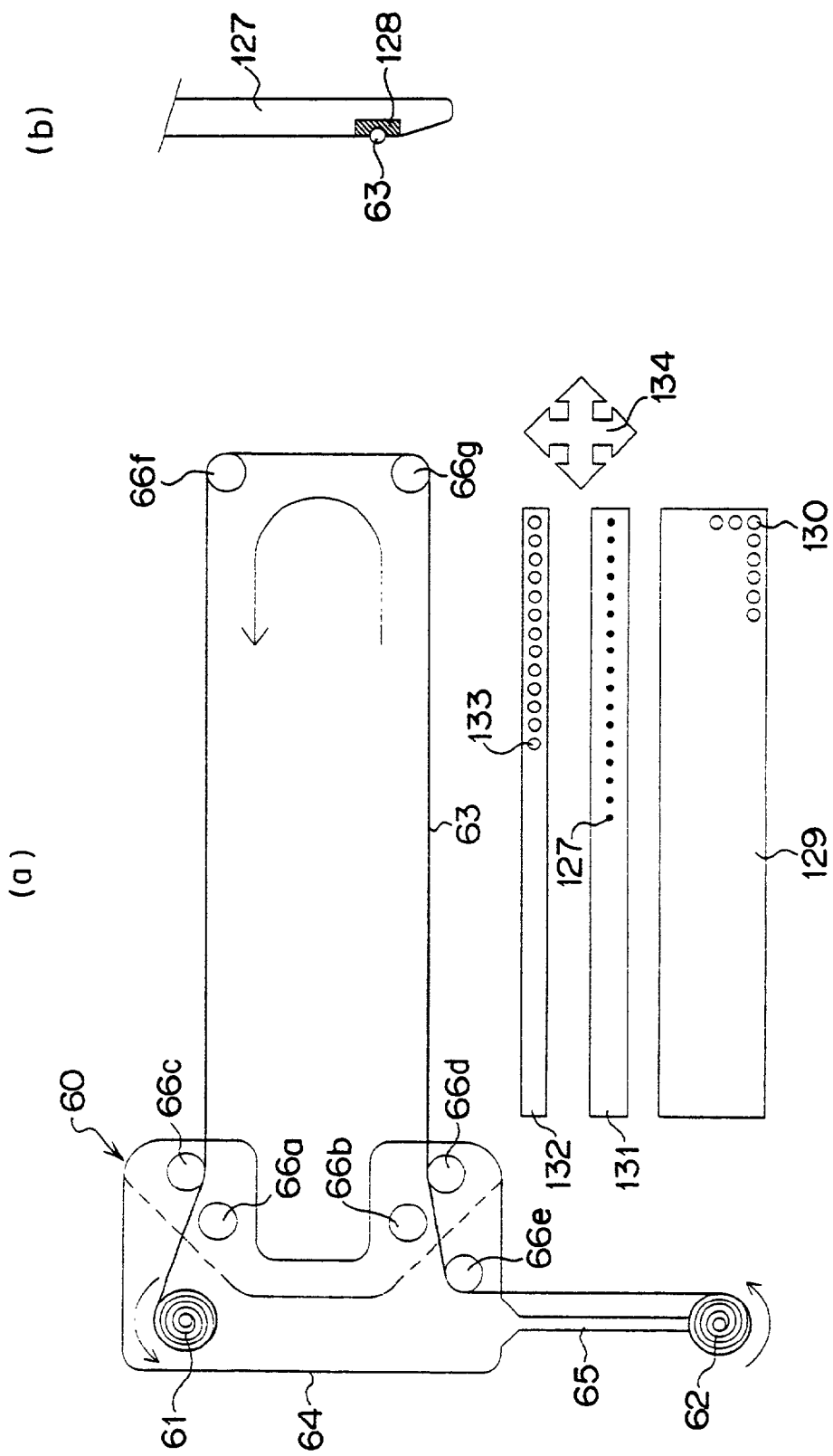
FIG. 13 is a plan showing an apparatus for making a support for substances for detection and a method of making a support for substances for detection of a thirteenth embodiment of the invention.

Next, an apparatus for making a support for substances for detection and a method of making a support for substances for detection of a thirteenth embodiment are explained based on FIG. 13.

The apparatus of the thirteenth embodiment is used for positioning the substances for detection on the base member 63 of the support for substances for detection 60 having a cassette-like supporting member.

As shown in FIG. 13(a), the apparatus comprises, a microplate-like vessel 129 having many wells 130 accommodating* suspensions respectively incorporating a variety of substances for detection such as oligonucleotides, a head 131 with a plurality of grooved needles 127 arranged in line, a cleaning tub 132 having cleaning sections 133 for cleaning the grooved needles 127, and a transfer device 134 movable in the X, Y, Z axes directions for transferring the head 131 between the microplate-like vessel 129, the cleaning tub 132 and a place where the base member 63 is extended.

Each cleaning section 133 of the cleaning tub 132 is provided so as to be able to individually remove used cleaning liquid and supply new cleaning liquid all the time (involving an overflow method).

FIG. 13(b) schematically shows a condition when the grooved needle 127 actually adheres the suspension incorporating the substances for detection onto the base member 63. In the figure, reference numeral 128 shows a groove formed in the grooved needle 127, where the suspension is held.

Though not shown in figure, the apparatus comprises a control section for controlling the transfer device 134. This control section comprises an information processing device having an input section for instructing an operation for inputting data by an operator, an output section for displaying or outputting a result of an operation and the contents of the instruction or data to the operator, a data storing device, and an arithmetic unit such as a CPU for analyzing the instructions of the operation, instructing each unit, displaying the results of the operation, and analyzing.

In order to adhere the substances for detection to the base member 63 using the apparatus, a feed pathway of the base member 63 that routes from the reel 62 around the rollers 66e, 66d, 66c mounted within the casing 64, and around the rollers 66f, 66g, to the reel 61, serving as the feed support section is set up.

Next, the head 131 is transferred to the microplate-like vessel 129 by instructing the transfer device 134. Then the grooved needles 127 are inserted into the wells simultaneously, so that the suspensions accommodated in the wells 30 are held by the grooves 128 of the needles 127. Thereafter, the head mounting the grooved needles 127 holding the suspension is transferred to the place where the base member 63 is stretched, and the grooves 128 of the needles 127 are brought into contact with the base member 63.

After completing the contact, the head 131 is transferred to the cleaning tub 132 by the transfer device 134, and each grooved needle 127 is inserted into each cleaning section 133 and cleaned. At this time, the base member 63 is fed by the length over which the suspension incorporating the substances for detection have been adhered by the head 131, by rotating the reel 61 of the cassette-like support for substances for detection. By repeating the above procedures, the substances for detection are positioned on the base member 63.

If the base member is tape-like and has a thickness of about 0.001 mm, a width of about 0.03 mm and a length of 1 m, and an interval between neighboring substances for detection of about 1 mm, then about 1000 substances for detection can be positioned in a projected area of 1 mm$^2$ with the base member integrated. Therefore, in the integrated state (though the integrated state is not always necessary) the base member has a high density of substances for detection of 1000/mm2. However, if the substances for detection are fixed on the surface of the base member (thickness about 0.03 mm, width about 0.001 mm, and length about 1 m), the surface area of the base member is about 60 mm$^2$, and the density is about 16/mm$^2$ which is low density. Therefore, in an expanded state, the positioning and fixation can be carried out at a lower density of about 1/60. This shows how easy it is to position the substances in an expanded state.

Figure 14:
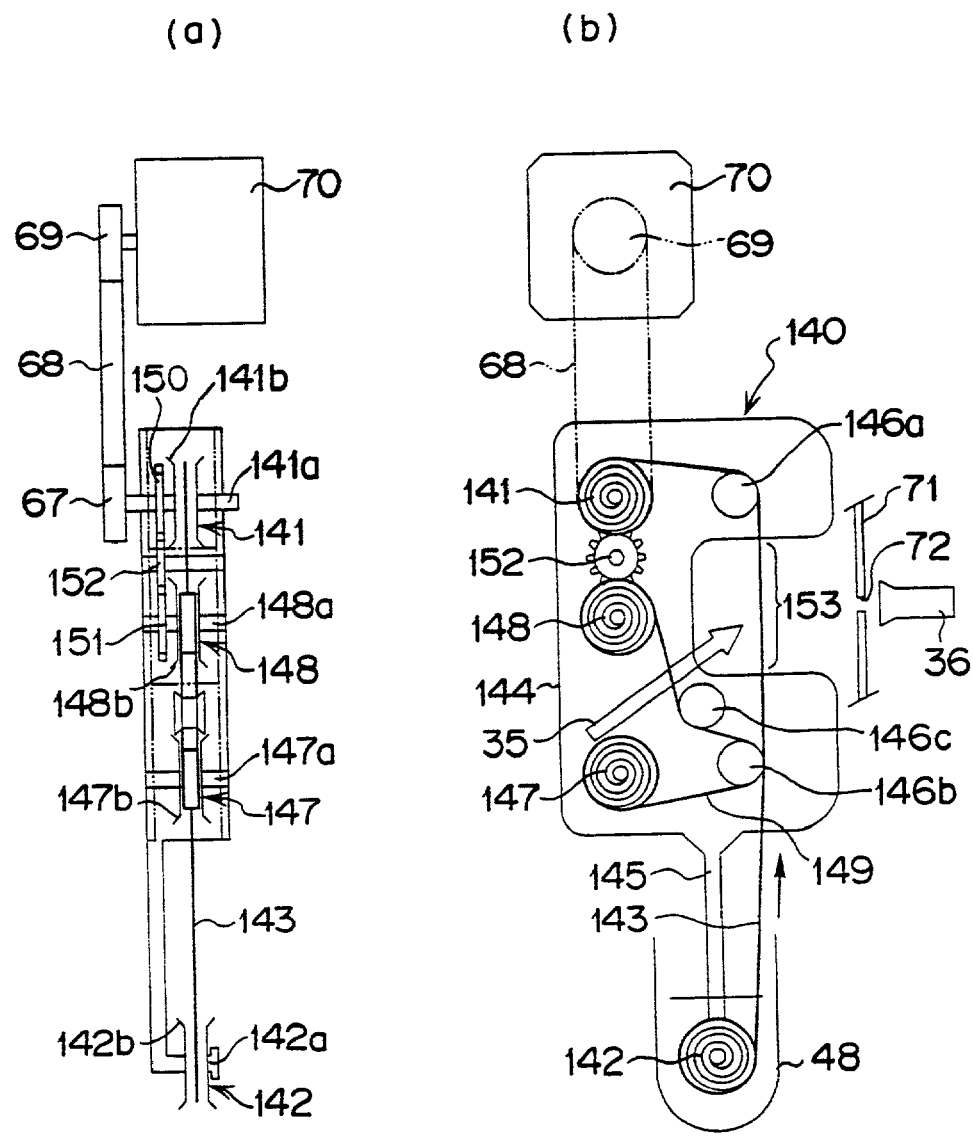
FIG. 14 is a plan showing a support for substances for detection of a fourteenth embodiment of the invention.

A support for substances for detection of a fourteenth embodiment is explained on the basis of FIG. 14. Since the same reference numeral as those in FIG. 7 denote the same parts, the explanation thereof is omitted.

As shown in FIG. 14(b), this support for substances for detection 140 comprises a take-up reel 141 and a supply reel 142 capable of taking up and supplying a base member 143, respectively. The base member 143 is routed between the take-up reel 141 and the supply reel 142, around the rollers 146a, 146b. In an initial state, the greater part of the base member 143 is wound on the take-up reel 142.

This support for substances for detection 140 further comprises two protection reels 147, 148. Between the protection reel 147 and the protection reel 148, a thin and slender protection band 149 having a width and a length larger than the width and length of the base member and made of flexible absorbable material such as paper or cloth is routed around a roller 146b and a roller 147. In an initial state, the greater part of the protection band 149 is wound on the protection reel 148.

Further, the support for substances for detection 140 comprises a casing 144 serving as the frame body, and a thin arm extending from the casing 144. The reels 141, 147, 148, and rollers 146a, 146b, 146c are rotatably mounted within the casing 144. The reel 142 is rotatably mounted on the lower end of the arm 145 in such a manner that enables insertion into the vessel 48 etc.

As shown in FIG. 14(a), the reels 141, 142, 147, 148 each comprise cylindrically formed cores 141a, 142a, 147a, 148a, and two guide frames 141b, 142b, 147b, 148b which are mounted on an opposite ends of the cores at a predetermined spacing and through which a liquid can be pass.

A coupling section for concentrically connecting with the outer gear 67, is mounted on the core 141a of the take-up reel 141. Further, a gear 150 is concentrically mounted and secured on the core 141a of the take-up reel 141. The gear 150 is mounted within the casing 144.

A gear 151 is concentrically mounted within the casing 144 on the core 148a of the protection reel 148 and secured thereto. The gear 150 and the gear 151 are connected through a gear 152 mounted within the casing 144. The tooth number of the gear 150 and the gear 151 are for example, made the same.

The take-up reel 141, the supply reel 142, the roller 146b, the roller 146a and the gears 150, 151, 152 correspond to the feed support section. The gear 67, a timing belt 68, a gear 69 and a motor 70 that are separated from the support for substances for detection 140, correspond to the feed mechanism.

In consideration of the support for substances for detection of the embodiment constructed as mentioned above, at an initial state, the base member 143 is wound on the take-up reel 142, and the protection belt 149 is wound on the protection reel 147. In this state, when the reel 141 is rotated by the motor 70, the base member 143 travels along the pathway from the reel 142, around the roller 146b and through the detection region 153 to the reel 141.

In this case, a torque from the motor 70 rotates the protection reel 148, through the gears 150, 152, 153, and feeds the protection belt 149 along the pathway from the reel 147, around the roller 146b and the roller 146c to the reel 148, with the speed substantially equal to that of the base member 143.

Therefore, since the protection belt 149 contacts with the base member 143 at the same speed and in such a manner that the belt 149 is sandwiched between the base member 143 and the roller 146b at the outer periphery of the roller 146b, rubbing generated by relative velocity between the base member 143 and the protection belt 149 can be avoided. Further, since the base member 143 does not contact with the roller 146b, cross contamination can be prevented.

Further, since the protection belt 149 can absorb the moisture adhered to the base member 143 and can dry the base member 143, reliable detection can be carried out in the detection region 153 through which the base member 143 passes after being dried. The reels 141, 142 and the rollers 146a, 146b, 146c correspond to the feed support section, and constitute the supporting member together with the frame body.

A spacer member of a fifteenth embodiment will now be explained based of FIG. 15. Since the same reference numerals as those already explained based on FIG. 14 indicate the same parts, explanation thereof is omitted.

FIG. 15(a) shows the spacer member 155 of the embodiment installed for instance, on the supply reel 142. FIG. 15(b) shows the spacer member 155 detached from the supply reel 142.

The spacer member 155 comprises a base 156, and four evenly spaced pins 157 projecting from the base 156. The spacer member 155 is installed in such a manner that the pins 157 pierce through four holes 158 provided in the one guide frame 142b, passes near the outer periphery of the core 142a and reaches four depressions formed in the other guide frame 142b. These four holes 158, four pins 157, and four depressions are respectively provided so as to subtend a central angle of 90° between each other.

As shown in FIG. 15(a), in order to use the spacer member 155, at first the spacer member 155 is installed bypassing the four pins through the four holes 158 made in the guide frame 142b. Then keeping that state, the base member 143 is wound in an aligned state, while being tensioned so as to wrap around the core 142a and the four pins 157.

After completing winding, as shown in FIG. 15(b), the spacer member 155 is detached from the reel 142 with the base member 143 being supported on the reel 142. Then, since tension imposed on the base member 143 is removed, the base member 143 is loosely wound on the core 142a.

With this embodiment, since sufficient space is generated around the base member 143, a suspension incorporating target substances can spread around the base member and reaction can be carried out uniformly. With this embodiment, the loose winding state can be obtained more easily than the case where the base member are wound without tension from the beginning.

The above mentioned embodiment is specifically explained for a complete and clear understanding of the invention. However, the appended claims are not to be thus limited. The appended claims can be construed as embodying all modifications and alternative constructions that may occur to one skilled in the art which fairly fall within the basic teaching herein set forth. For instance, with the above embodiments, the case when the substances for detection are oligonucleotides, and the target substance is DNA fragments is explained. However, the cases of other biopolymers such as genetic substances, proteins, amino-acids, immune substances, or sugars are not excluded.

Constituents, substance, apparatus, components, or steps can be combined arbitrarily while making appropriate changes. Further, with the above embodiment, analysis of the target substances has only been explained for the case where these are marked by a fluorescent substance. However, the invention is not limited to this case. For example, analysis of the target substance may be carried out by using such substances for detection that are adhered to polystyrene minute particles of substantially the same size lined up and fixed to the base member, and covered with gold on only the upper hemisphere by vacuum deposition. In this case, when the substances for detection are brought into contact with the suspension incorporating the target substances, the color of the particles are changed by combination with the target substances, while a white light is irradiated into the surface. Therefore, analysis of target substances can be carried out on the basis of detected color.

Furthermore, though the base member whose cross section is substantially circular has been explained, the invention is not limited to the case. For instance, a tape-like base member is also possible.

With the above mentioned embodiments, though only the case where the substances for detection are positioned by attaching the liquid holding tip to the base member is disclosed, the invention is not limited to the case. For instance, the substances for detection can of course be positioned by using a dispensing device or a printing device, naturally.

Furthermore, with the above embodiments, the case where the detection is carried out by irradiating the excitation light from the light source is described. However the invention is not limited to the case. For instance, the case where irradiation of the excitation light is not necessary is also possible.

In order to make the reel on which the base member is wound, for instance, each suspension incorporating each type of substance for detection is dispensed, painted, imprinted, written or printed on a film, without contacting each other, in many thin parallel lines, by using the apparatus for making the support for substances for detection. The film on which the substances are fixed, is then rolled onto a cylindrical core in the direction perpendicular to the lines to integrate the substances. The rolled film is then severally sliced for each core, in a direction perpendicular to the axis of the core. Guide frames are then fitted to the resultant sliced rolled film to thereby give reels wound with base members. By mounting the reel to the frame body, supports for substances for detection having cassette-like or cartridge-like supports for substances for detection can thus be easily obtained in large quantities and at low cost.

What is claimed is:

1. A support for substances for detection comprising:
   a flexible base member formed to be slender like a thread, string or tape;
   a variety of substances for detection having predetermined chemical structure and being fixed side by side along the length of the base member; and
   a supporting member for supporting the base member in a manner that enables expansion,
      said supporting member comprising a frame body, and a feed support section mounted on said frame body for supporting said base member in a manner that enables feeding, wherein said feed support section comprises a drum rotatably mounted on said frame body and threaded around a periphery thereof, and said frame body has an arm for enabling said base member to be inserted into a vessel outside of said support for substances for detection, and said base member is wound along a bottom of the thread of said drum and can be moved in the neighborhood of a tip end of said arm by rotating said drum;
   said base member being supported by said feed support section so as to be able to travel along a defined feed pathway;
   wherein a fixed location of each substance for detection corresponds with the chemical structure thereof.

2. A support for substances for detection comprising:
   a flexible base member formed to be slender like a thread, string or tape;
   a variety of substances for detection having predetermined chemical structure and being fixed side by side along the length of the base member; and
   a supporting member for supporting the base member in a manner that enables expansion, said supporting member comprising:
      a frame body, and a feed support section mounted on said frame body for supporting said base member in a manner that enables feeding,
      said base member being supported by said feed support section so as to be able to travel along a defined feed pathway;
         wherein said feed support section comprises a supply reel and a take-up reel having a core around which said base member can be wound, and two guide frames through which liquid can pass mounted on opposite ends of said core, and said two reels are rotatably mounted on said frame body, and said frame body has an arm for enabling said base member to be inserted into a vessel outside of said support for substances for detection, and said base member is routed between two reels so as to pass around the tip end of said arm;
   wherein a fixed location of each substance for detection corresponds with the chemical structure thereof.

3. A support for substances for detection according to claim 1 or 2, wherein one or more marks are provided on said base member to indicate a reference position.

4. A support for substances for detection according to claim 1 or 2, wherein said base member is supported by said supporting member, while being enclosed in a defined area so that said base member can contact with a liquid, and can be expanded from the area.

5. A support for substances for detection according to claim 4, wherein said supporting member is made of a permeable material having a plurality of pores.

6. A support for substances for detection according to claim 5, wherein said supporting member comprises a spacer member for generating a space around said base member when said base member is integrated and supported.

7. A support for substances for detection according to claim 1 or 2, wherein said supporting member comprises a reel, and said reel comprises a core on which said base member is wound, and two guide frames mounted on opposite ends of said core facing one another and through which a liquid can pass.

8. A support for substances for detection, according to claim 2, wherein said frame body comprises a casing, and an arm outwardly extending from said casing, and said take-up reel is rotatably mounted on said casing, and said supply reel is rotatably mounted on the tip end section of said arm.

9. A support for substances for detection according to claim 1 or 2, wherein said feed support section comprises one or more rollers rotatably mounted on said frame body along said feed pathway.

10. A support for substances for detection according to claim 9, comprising a protection belt sandwiched between said roller and said base member at the periphery of said roller, that travels at a predetermined feed velocity.

11. A support for substances for detection according to claim 1 or 2, comprising a detection region and/or a reaction region, on said feed pathway of said base member, wherein said detection region is one where substances for detection are detected, and said reaction region is one where the reaction between the substances for detection and the target substances is carried out.

12. A support for substances for detection according to claim 1 or 2, wherein said feed support section comprises a coupling for connecting with an outer feed mechanism for feeding said base member.

13. A support for substances for detection comprising:
   a flexible base member formed to be slender like a thread, string or tape;
   a variety of substances for detection having predetermined chemical structure and being fixed side by side along the length of the base member; and
   a supporting member made of a permeable material having a plurality of pores and adapted to support the base member, said supporting member comprising:
     a core on which said base member is wound, and
     two guide frames mounted on opposite ends of said core facing one another and through which a liquid can pass; and
     detachable spacer pins provided so as to pierce through holes in one guide frame, pass near an outer periphery of said core and reach the other guide frame for generating a space around said base member;
   said base member being enclosed in a defined area so that said base member can contact with a liquid, and can be expanded from the area;
   wherein a fixed location of each substance for detection corresponds with the chemical structure thereof.

* * * * *